US006730305B1

(12) United States Patent
Wertz et al.

(10) Patent No.: US 6,730,305 B1
(45) Date of Patent: May 4, 2004

(54) NUCLEOTIDE SEQUENCES ENCODING BOVINE RESPIRATORY SYNCYTIAL VIRUS IMMUNOGENIC PROTEINS

(75) Inventors: Gail W. Wertz, Birmingham, AL (US); Robert Lerch, Madison, WI (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/567,458

(22) Filed: May 8, 2000

(51) Int. Cl.[7] ............................................. A61K 39/155
(52) U.S. Cl. ................................ 424/211.1; 424/204.1; 435/69.3; 435/320.1; 435/325; 435/173.3; 435/236; 530/403
(58) Field of Search ......................... 424/211.1, 204.1; 435/69.3, 320.1, 325, 173.3, 236; 530/403; 536/231

(56) References Cited

U.S. PATENT DOCUMENTS

| | | | |
|---|---|---|---|
| 4,563,419 A | 1/1986 | Ranki et al. | |
| 4,708,871 A | 11/1987 | Geysen ........................ | 424/88 |
| 4,722,848 A | 2/1988 | Paoletti et al. ................ | 424/89 |
| 4,752,638 A | 6/1988 | Nowinski et al. | |
| 4,790,987 A | 12/1988 | Compans et al. | |
| 4,855,224 A | 8/1989 | Berman et al. | |
| 4,879,213 A | 11/1989 | Fox et al. ...................... | 435/5 |
| 4,994,368 A | 2/1991 | Goodman et al. | |
| 5,223,254 A | 6/1993 | Paradiso et al. | |

FOREIGN PATENT DOCUMENTS

| | | |
|---|---|---|
| WO | WO 87/04185 | 7/1987 |
| WO | WO 89/02935 | 4/1989 |
| WO | WO 92/07940 | 5/1992 |

OTHER PUBLICATIONS

Amann et al. "Bovine respiratory syncytial virus nucleocapsid protein: mRNA sequence analysis and expression from recombinant vaccinia vectors." J. Gen. Virol. 73, 999–1003 (1992).
Wertz et al. Workshop on "reverse genetics of negative stranded RNA viruses" sponsored by the Juan March Institute, Madrid, Spain. Virus Research 30, 215–219 (1993).
Lerch et al. "Nucleotide sequence analysis and expression from recombinant vectors demonstrate that the attachment protein G of bovine respiratory syncytial virus is distinct from that of human respiratory syncytial virus." J. of Virol. 64(11):5559–5569 (1990).
Lerch et al. "Nucleotide sequence analysis of bovine respiratory syncytial virus fusion protein mRNA and expression form a recombinant vaccinia virus." Virology 181:118–131 (1991).
Samal et al. "Molecular cloning and sequence analysis of bovine respiratory syncytial virus mRNA encoding the major nucleocapsid protein." Virology 180:453–456 (1991).
Geysen et al. "Use of peptide synthesis to probe viral antigens for epitopes to a resolution of a single amino acid." Proc. Natl. Acad. Sci. USA 81:3998–4002 (Jul. 1984).
Ward et al. "Antigenic and Structural Variation in the Major Nucleocapsid Protein of Respiratory Syncytial Virus." J. Gen. Virol. 65:1749–1757 (1984).
Van Regenmortel (Ed.) "Structure of Antigens" vol. 1. CRC Press, Inc., Boca Raton, Florida (1992); see Chapter 1, pp. 1–27.
Collins et al. "The envelope–associated 22K protein of human respiratory syncytial virus: Nucleotide sequence of mRNA and a related polytranscript." J. of Virol. 53:65–71 (1985).
Collins et al. "Identifcation of a tenth mRNA of respiratory syncytial virus and assignment of polypeptides to the 10 viral genes." J. of Virol. 49:572–578 (1984).
Kubota et al. "Establishment of attenuated strain of bovine respiratory syncytial virus for live cattle vaccine." Japanese J. of Vet. Sci. 52:695–704 (1990).
Nicholas et al. "Mapping an antibody–binding site and a T–cell–stimulating site on the 1A protein of respiratory syncytial virus." J. of Virol. 62:4465–4473 (1988).
Baker et al. Am. J. Vet. Res. 46:891–892 (1985).
Cash et al. Virology 82:369–379 (1977).
Kimmon et al. Vet. Q. 11:250–253 (1989).
Kimmon et al. J. Clinical Microbiol. 25:1097–1106 (1987).
Lerch et al. "Characterization of bovine respiratory syncytial virus proteins and mRNAs and generation of cDNA clones to the viral mRNAs." J. Virol. 63:833–840 (1989).

(List continued on next page.)

Primary Examiner—Laurie Scheiner
(74) Attorney, Agent, or Firm—Gifford, Krass, Groh, Sprinkle, Anderson & Citkowski, P.C.

(57) ABSTRACT

The present invention relates to recombinant DNA molecules which encode bovine respiratory syncytial (BRS) virus proteins, to BRS virus proteins, and peptides and to recombinant BRS virus vaccines produced therefrom. It is based, in part, on the cloning of substantially full length cDNAs which encode the entire BRS virus G, F, and N proteins. According to particular embodiments of the invention, DNA encoding a BRS virus protein or peptide may be used to diagnose BRS virus infection, or, alternatively, may be inserted into an expression vector, including, but not limited to, vaccinia virus as well as bacterial, yeast, insect, or other vertebrate vectors. These expression vectors may be utilized to produce the BRS virus protein or peptide in quantity; the resulting substantially pure viral peptide or protein may be incorporated into subunit vaccine formulations or may be used to generate monoclonal or polyclonal antibodies which may be utilized in diagnosis of BRS virus infection or passive immunization. In additional embodiments, BRS virus protein sequence provided by the invention may be used to produce synthetic peptides or proteins which may be utilized in subunit vaccines, or polyclonal or monoclonal antibody production. Alternatively, a nonpathogenic expression vector containing the genes, parts of the genes, any combination of the genes, or parts thereof may itself be utilized as a recombinant virus vaccine.

3 Claims, 26 Drawing Sheets

OTHER PUBLICATIONS

Figure 1:
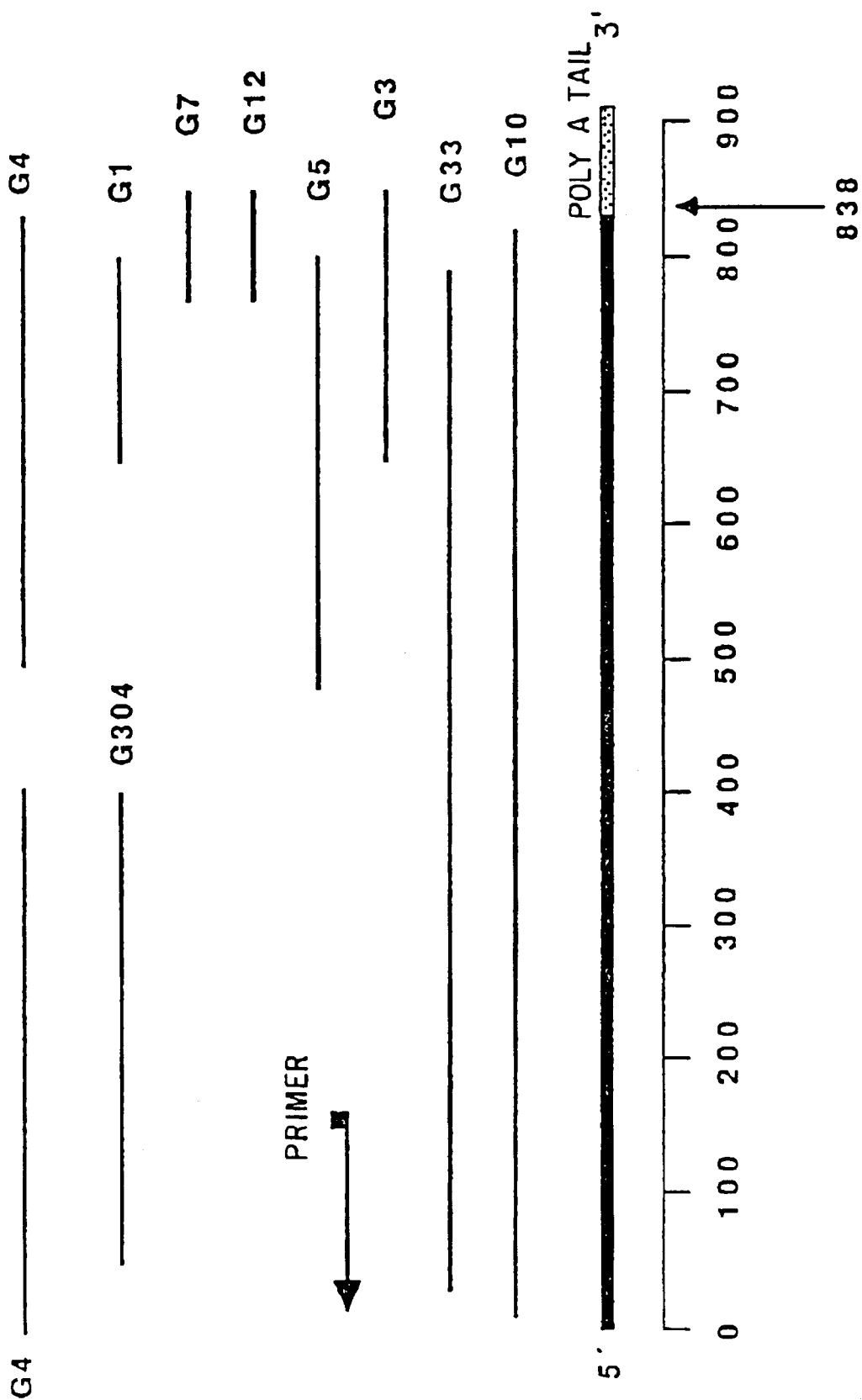

Orvell et al. "Preparation and Characterization of Monoclonal Antibodies Directed Against Five Structural Components of Human Respiratory Syncytial Virus Subgroup B." J. Gen. Virol. 68:3125–3135 (1987).

Park et al. Res. Rep. Rural Dev. Adm. 31:24–29 (English abstract) (1989).

Stott et al. J. Hyg.; Camb. 93:251–261 (1984).

Trudel et al. Vaccine 7:12–16 (1989).

Bowie et al. Science 247:1306–1310 (1990).

Kumar et al. PNAS 87:1337–1341 (1990).

Berzotsky. Science 229:932–940 (1985).

Stern. TIBTECH 9:163–167 (1991).

Kennedy et al. T. Gen. Virol. 69(12):3023–3032 (1988).

Young and Davis. PNAS 80:1194–98 (1983).

Sambrook et al. Molecular Cloning A Laboratory Manual. See Chapters 1.1–1.20, 17.1–17.16 and 17.37–17.41.

```
A2           G         AC          AA C AGG C A GC CCGCT         G A   AC   G CA TCTC  TC  80
Bovine NGGGCAAATACAAGTATCTCCAACCATACCCATCATCTTAAATTCAAGACATTAAAGAGGGCTTGGAAAGCCTCAAAATA 80
18537  NNNNN      G     CC         A C AGA    A GC CTGC  G   TC TG A A A C   G TA TCTT  TC  80

A2      T  AT   T CAT  C   G   C       A   C T       TG A CA       TCA A  A         TT  G       160
Bovine CTTTATATAGTAGGATTATCATGTTTATATAAGTTCAATTTAAAAATCCCTTGTCCAAACGGCTTTGTCCACCCTAGCAATGA 160
18537  TC A  T   AT CC  T       C GA  A           TA A CA    TA  AC    AGTTT G          160

A2      T  CA   T        TA A  TG       C AT     AGCCTC   C   CCAC      T  CA  A    A TGC ATC 240
Bovine TAACCTGACATCACTCGTCATCACAGCCATTATTACATTAGTGTGGAAATGCTAAAGCCAAGCCCACATCCAAAACCA 240
18537  T  CA C   T  AA TG         A A T   C TCTCT CC       CAC     TT CA TA   A GGTTA     240

A2             TACAAG TGC    AGC     AT A G   ACA    C A    ACC       CC  A TCCTC GCTTGG   TCAGTC  C       320
Bovine ACCATCCAACAACAACAGCCCCAAAACCAGCCCATCCACCATTTTCACAGAGCACTACAAATCAACTCACACATC 320
18537  GTTCAAAC AT   A A C   CA TG       AA C T   CA C ACC T  TC AGT CCACCAG  AGGGTCA  T       320

A2       T A  CGTCTGAA TTACA    A   A CACC  C     CTAG  TA ....C AC  CAGGA       AGTC A CCT C    396
Bovine AATTCAAAGCACCACCACTGTCCAACTACTAAACATAGACACTACTAGAGGAATTACATATGGTCACTCAACCAACGAAA 400
18537  C AA    CC      A  CACA  A C A AC  CA ATTCAG  C A ....T  C  CA ATACA AATC GA    AC C 396
```

FIG. 2A

```
A2          T  C     TC  GA C  AAA  CAAC A A      A A ACAAC        C  G  CA CA   A A CGCCA  A  A476
Bovine CCCAAAACAGAAAAATCAAAGGCCA...ATCCACTCTACCCGGCCACCAGAAACCACCAATCAATCATCGGGAAGCAT 476
18537       AT C     CC A C A G  GAATCA       TC A ACAG        AC  G  AGC CA  AT  CGTTC   AA A476

A2         A  A  AAGC  A CCA TA TG TTTTC       TG GTGT AA  T  A  C        C  T    CAGCAAC        CAA 556
Bovine CCCCCCTGAAAACCATCAAGACCACACAACTTCCAAACACTCCCTATGTGCCTTGCAGTACATGTGAAGTAATCTTG 556
18537  T  A  AA    A CAA       TG TT  C T   TG GTGT AAT T       T   T                GTAA    AAC 556

A2        C     GGG TA      A A GAATAC AA C A AA      G,A AGAAAA C  T C  AG C    A AA       CC 636
Bovine CTTGCTTATCACTCTGCCATATTGAGACGGAGAGCACCAAGCAGAGCCCTACAATCACCCTCAAAAGACTCCAAAA 636
18537  TC     AA    CA     A A CAATAC AAGC ACAA       AG A AAA  A  C     AA C    C AA       CC 636

A2         T   ...G  A C     AGATC       A CTC A C   C AA T  A  G AGTA   ACC  C A GC CA  GAAG 713
Bovine CCCAA...AACCACTAAAAA....GCCAACCAAGACAACAATCCACCAGAACCCTGAAACCAAACTGCAACCTA 709
18537  A            AACC  A AC    GAGACC       AAC CCAGC    AATG    A A  AG AAT ATC C A CC A     AAA 716

A2      GCC ACCAT    A  C A   A     ACATCAT A TA A  A TCACCTC   A    CAC GGA       C GA CT        A793
Bovine AAAACAACAACAGCAACTCCACAACAA....GGCATCCTCCTCTTCAACAGAACATCACACAATCAATCAACTA..CACAG 783
18537  CC ACC T   AG C A AGA  G GACACCAGCATT  A AATCCACCGTGC   GACAC     C  C AA TA        A 796
```

FIG. 2B

```
A2      G    A  ATGGA AC T     CTC    T  CTCCG AG CAA CC AGCCC   C CAAGTCTCTACAACATCCGAGTACCCA 873
Bovine ATC             TAG CAACACACCTCCATATAACATCTAATTATNGTTCTATATAGTTATTT..................  838
18537   TC A  CAGCA TC      CTC    CA CTCCG AAACA ACCCAGCTCCACACAAATACCCACAGCATCCGAGCCCTCC 876

A2     TCACAACCTTCATCTCCACCCAACACACCGGCCAG TAGTTACTT 918
Bovine .................................... ........
18537  ACATTAAAATCCTAAT TAA AAAACCTAGTCACATGCTTAGTTATTC 921
```

FIG. 2C

```
A2       T*WAI*KRIPNKK*GKKT*TKPT*K*TL***-**DP*PQTTKSKEVP*TKPTEEP*INTT    239
Bovine   ACLSLCHIETERAPSRAPTITLKKTPKPKTT-KKPTKTTIHHRTSPETKLQPKNNTATPQ    239
18537    L*K*I*KTIPSNK*KKK***KPTNK*TT***N*RDP**PAKMPKKEIITNPA*KP*LKTT    240

A2       KTNIIT*LLTS*TTGNPELTSQMETFHSTSSEGNPSPSQVSTTSEYPSQPSSPPNTPRQ    298
Bovine   QGILSSTEHHTNQSTTQI                                            257
18537    ERDT*ISQSTVLDTI*PKYTIQQQSLHSTTSENTPSSTQIPTASEPSTLNPN         292
```

FIG. 3B

M

VV rVVG

PHASE CONTRAST

FLUORESCENT

```
GTATCTGTTGGTAACACACTATATTATGTAAATAAGCTAGAGGGAAAGCACTCTATATAAAGGGTGAACCAATTATTAATTACT 1445
ValSerValGlyAsnThrLeuTyrTyrValAsnLysLeuGluGlyLysAlaLeuTyrIleLysGlyGluProIleIleAsnTyrT 478

ATGATCCACTAGTGTTCCTTCGATGAGTTTGATGCATCAATTGCCCAAGTAAATGCAAAATAACCAAAGCCTGGCTTTCAT 1530
yrAspProLeuValPheProSerAspGluPheAspAlaSerIleAlaGlnValAsnAlaLysIleAsnGlnSerLeuAlaPheIl 506

ACGTCGATCTGATGAGTACTTCACAGTGTAGATGTAGGAAAATCCACCACAAATGTAGTAATTACTACTATTATTATAGTGATA 1615
eArgSerAspGluLeuLeuHisSerValAspValGlyLysSerThrThrAsnValValIleThrIleIleIleVallle 534

GTTGTAGTGATATTAATGTTAATAGCTGTGTAAGACCAGGAGTACTCCTATCATGCTAGGAAAGGATC 1700
ValValIleLeuMetLeuIleAlaValGlyLeuLeuPheTyrCysLysThrArgSerThrProIleMetLeuGlyLysAspG 563

AGCTTAGTGGTATCAACAATCTTTCCTTTAGTAAATGAAATGCATAATGTTTACAATCTAAACCTCAGAATCATAAATGTGATGA 1785
lnLeuSerGlyIleAsnAsnLeuSerPheSerLysEnd 574

GCTAAATTATTAATACATTCAAAAGTTCTATCCGCCAAGACCTGCATTTTTTATCAGTCTTATATAAGCTAACCTTACATGC 1870

TACACTCAGCTCCATGTTGATAGTTATAT 1899
```

FIG. 9C

```
                                                                              I              N  KE  K  NG  A
A2      ELLILKANAITTILTLTAVTFCFASG                              K             I              N  KE  K  NG  A
Long    ELPILKANAITTILAAVTFCFASS                                K             I              N  KE  K  NG  A
RSS-2   ELPILKTNAITAILTAVTLCFASG                                K             I              N  KETK  NG  T
18537   ELLIH SSAIFLTLAVNALYL SS                                      F
Bovine  MAATAMRMIISIFIFISTYMTHITLCQNITEEFYQSTCSAVSRGYLSALRTGWYTSVVTIELSKIQKNVCKSTDSK 75
                                                                     ▲
                                  DK  K   T    L   ST PTNN  R  EL REMN  L NA KINVTLS        V  I
                                  DK  K   T    L   ST ANN   R  EL REMN    N KINVTLS         V  I
                                  DK  KS  T    L   ST TNN   R  EL REMN    N NTNVTLS         V  I
                                  DK  K   T    L   T  ANN   R  EA QYMN    T NINDSIS         V  I
       76 VKLIKQELERYNNAVIELQSLMQNEPASF SRAKRGIPELIHYTRNSIKRFYGLMGKKRKRRFLGFLLGIGSAVAS 150
                                                                   ▲
              V                                                        Q   I  KQS  S
       T      V                                                        Q   I  KQS  S
       I      V                                              S         Q   I  KQS  S
       I      V                                              S         Q   I  QQS  T
              G                                              S  NNR                         ▲
       151 GVALSKVLHLEGEVNKIKNALLSTNKAVVSLSNGVSVLTSKVLDLKNYIDKELLPKVNNHDCRISNIETVIEFQQ 225
```

451 SVGNTLYYVNKLEGKALYIKGEPIINYYDPLVFPSDEFDASIAQVNAKINQSLAFIRRSDELLHSVDVGKSTTNV 525

M  I IL S   L A   VT S    IA  N
    M  I IL S   L A   VT S    IA  N
    M  I IL S   L A   VT S    IA  N
    M  I L  S I L AKN VT S    IA

526 VITTIIIVVVIILMLIAVGLLFEYCKTRSTPIMLGKDQLSGINNLSFSK 574
```

FIG. 11C

M

VV rVVF

PHASE CONTRAST    FLUORESCENT

```
  1  CAAAAATGGC TCTTAGCAAG GTCAAACTAA ATGCACTTT  CAACAAGGAC
 51  CAACTGTTGT CAACCAGCAA ATATACTATT CAACGTAGTA CAGGTGACAA
101  CATTGATATA CCCAATTACG ATGTGCAAAA ACATCTCAAT AAGTTGTGTG
151  GTATGCTATT AATAACAGAA GATGCCAATC ATAAATTTAC AGGACTGATA
201  GGTATGTTAT ATGCTATGTC CCGATTGGGG AGAGAAGATA CCCTTAAAAT
251  ACTCAAAGAT GCAGGCTACC AAGTGAGGGC CAATGGGGTT GATGTGATAA
301  CACATCGACA GGATGTGAAT GGAAAAGAAA TGAAATTTGA AGTGCTAACA
351  TTAGTCAGCT TAACATCAGA AGTTCAAGGT AATATAGAAA TAGAGTCAAG
401  GAAGTCTTAC AAAAAGATGC TAAAAGAGAT GGGAGAGGTA GCTCCAGAAT
451  ACAGACATGA CTtCCTGAT  TGTGGTATGA TAGTGCTATG TGTTGCTGCT
501  TTGGTTATAA CAAAATTAGC AGCAGGTGAT AGGTCAGGCC TCACTGCAGT
551  CATTAGGAGA GCCAACAATG TACTAAGGAA TGAAATGAAA CGATACAAAG
601  GACTCATCCC GAAAGATATA GCCAACAGCT TCTATGAAGT ATTGAAAAG
```

FIG. 17A

```
 651  TACCCTCATT ACATAGATGT ATTCGTACAT TTTGGCATTG CTCAATCCTC
 701  AACTAGAGGA GGTAGTAGGG TAGAAGGAAT CTTTGCAGGG TTATTCATGA
 751  ATGCATATGG AGCAGGTCAA GTGATGTTAA GATGGGGTGT GCTAGCCAAA
 801  TCAGTCAAGA ACATTATGCT TGGTCATGCC AGCGTACAAG CAGAAATGGA
 851  ACAGGTTGTA GAAGTCTATG AATATGCACA AAAGTTAGGT GGAGAAGCTG
 901  GTTTTATCA  CATACTGAAC ATCCTAAAG  CATCATTGTT ATCCTTGACA
 951  CAATTCCCCA ACTTCTCTAG TGTAGTCCTA GGCAATGCTG CAGGACTAGG
1001  TATAATGGGT GAGTATAGAG GTACACCAAG AAACCAAGAC TTGTATGATG
1051  CTGCCAAAGC ATATGCAGAA CAACTAAAAG AGAATGGGGT CATCAATTAC

1101  AGTGTGTTGG ATCTGACTAC AGAGGAATTA GAGGCAATCA AGAACCAATT
1151  GAATCCCAAA GATAATGATG TGGAATTGTG AGTTAATAAA AAAA
```

FIG. 17B

1    KMALSKVKLN DTFNKDQLLS TSKYTIQRST GDNIDIPNYD VQKHLNKLCG
51   MLLITEDANH KFTGLIGMLY AMSRLGREDT LKILKDAGYQ VRANGVDVIT
101  HRQDVNGKEM KFEVLTLVSL TSEVQGNIEI ESRKSYKKML KEMGEVAPEY
151  RHDFPDCGMI VLCVAALVIT KLAAGDRSGL TAVIRRANNV LRNEMKRYKG
201  LIPKDIANSF YEVFEKYPHY IDVFVHFGIA QSSTRGGSRV EGIFAGLFMN
251  AYGAGQVMLR WGVLAKSVKN IMLGHASVQA EMEQVVEVYE YAQKLGGEAG
301  FYHILNNPKA SLLSLTQFPN FSSVVLGNAA LTTEELEAIK NQLNPKDNDV
351  AKAYAEQLKE NGVINYSVLD LTTEELEAIK NQLNPKDNDV EL*VNKK

FIG. 18

NUCLEOTIDE SEQUENCES ENCODING BOVINE RESPIRATORY SYNCYTIAL VIRUS IMMUNOGENIC PROTEINS

1. INTRODUCTION

The present invention relates to recombinant DNA molecules which encode bovine respiratory syncytial (BRS) virus proteins as well as corresponding BRS virus proteins and peptides derived therefrom. It is based, in part, on the cloning of full length cDNAs encoding a number of bovine respiratory syncytial virus proteins, including, F, G, and N. DNAs encoding the G and F proteins have been inserted into vaccinia virus vectors, and these vectors have been used to express the G and F proteins in culture and G protein encoding vectors have been used to induce an anti-bovine respiratory syncytial virus immune response. The molecules of the invention may be used to produce safe and effective bovine respiratory syncytial virus vaccines.

2. BACKGROUND OF THE INVENTION

2.1. Bovine Respiratory Syncytial Virus

Bovine respiratory syncytial (BRS) virus strain 391-2 was isolated from an outbreak of respiratory syncytial virus in cattle in North Carolina during the winter of 1984 to 1985. The outbreak involved five dairy herds, a beef calf and cow operation, and a dairy and steer feeder operation (Fetrow et al., North Carolina State University Agric. Extension Service Vet. Newsl.).

Respiratory syncytial virus, an enveloped, single-stranded, negative-sense RNA virus (Huang and Wertz, 1982, J. Virol. 43:150–157; Kingsbury et al., 1978, Intervirology 10:137–153), was originally isolated from a chimpanzee (Morris, et al., 1956, Proc. Soc. Exp. Biol. Med. 92:544–549). Subsequently, respiratory syncytial virus has been isolated from humans, cattle, sheep and goats (Chanock et al. 1957, Am. J. Hyg. 66:281–290; Evermann et al., 1985, AM. J. Vet. Res. 46:947–951; Lehmkuhl et al., 1980, Arch. Virol. 65:269–276; Lewis, F. A., et al., 1961, Med. J. Aust. 48:932–33; Paccaud and Jacquier, 1970, Arch. Gesamte Virusforsch 30:327–342). Human respiratory syncytial (HRS) virus is a major cause of severe lower respiratory tract infections in children during their first year of life, and epidemics occur annually (Stott and Taylor, 1985, Arch. Virol. 84:1–52). Similarly, BRS virus causes bronchiolitis and pneumonia in cattle, and there are annual winter epidemics of economic significance to the beef industry (Bohlender et al., 1982, Mod. Vet. Pract. 63:613–618; Stott and Taylor, 1985, Arch. Virol. 84:1–52; Stott et al., 1980, J. Hyg. 85:257–270). The highest incidence of severe BRS virus-caused disease is usually in cattle between 2 and 4.5 months old. The outbreak of BRS virus strain 391-2 was atypical in that the majority of adult cows were affected, resulting in a 50% drop in milk production for one dairy herd and causing the death of some animals, while the young of the herds were only mildly affected (Fetrow et al., 1985, North Carolina State University Agric. Extension Service Vet. Newsl.).

BRS virus was first isolated in 1970 (Paccaud and Jacquier, 1970, Arch. Gesamte Virusforsch. 30:327–342), and research has focused on the clinical (van Nieuwstadt, A. P. et al., 1982, Proc. 12th World Congr. Dis. Cattle 1:124–130; Verhoeff et al., 1984, Vet. Rec. 114:288–293) and pathological effects of the viral infection on the host (Baker et al., 1986, J. Am. Vet. Med. Assoc. 189:66–70; Castleman et al., 1985, Am. J. Vet. Res. 46:554–560; Castleman et al. 1985, Am. J. Vet. Res. 46:547–553) and on serological studies (Baker et al., 1985, Am. J. Vet. Res. 46:891–892; Kimman et al., 1987, J. Clin. Microbiol. 25:1097–1106; Stott et al., 1980, J. Hyg. 85:257–270). The virus has not been described in molecular detail. Only one study has compared the proteins found in BRS virus-infected cells with the proteins found in HRS virus-infected cells (Cash et. al., 1977, Virology 82:369–379). In contrast, a detailed molecular analysis of HRS virus has been undertaken. cDNA clones to the HRS virus mRNAs have been prepared and used to identify 10 virus-specific mRNAs which code for 10 unique polypeptides, and the complete nucleotide sequences for 9 of the 10 genes are available (Collins, P. L., et al., 1986, in "Concepts in Viral Pathogenesis II," Springer-Verlag., New York; Stott and Taylor, 1985, Arch. Virol. 84:1–52).

Two lines of evidence suggest that HRS virus and BRS virus belong in distinct respiratory syncytial virus subgroups. First, BRS virus and HRS virus differ in their abilities to infect tissue culture cells of different species (Paccaud and Jacquier, 1970, Arch. Gesamte Virusforsch. 30:327–342). With one exception, studies have shown that BRS virus exhibits a narrower host range than HRS virus. Matumoto et al. (1974, Arch. Gesamte Virusforsch. 44:280–290) reported that the NMK7 strain of BRS virus has a larger host range than the Long strain of HRS virus. Others have been unable to repeat this with other BRS strains (Paccaud and Jacquier, 1970, Arch. Gesamte Virusforsch. 30:327–342; Pringle and Crass, 1978, Nature (London) 276:501–502). The second line of evidence indicating that BRS virus differs from HRS virus comes from the demonstration of antigenic differences in the major glycoprotein, G, of BRS virus and HRS virus (Orvell et al., 1987, J. Gen. Virol. 68:3125–3135). Studies using monoclonal antibodies have grouped HRS virus strains into two subgroups on the basis of relatedness of the G glycoprotein (Anderson 1985, J. Infect. Dis. 151:626–633; Mufson, et al., 1985, J. Gen. Virol. 66:2111–2124). The G protein of BRS virus strains included in these studies did not react with monoclonal antibodies generated against viruses from either HRS virus subgroup (Orvell et al., 1987, J. Gen. Virol. 68:3125–3135).

BRS virus provides an opportunity to study the role of the major glycoprotein, G, in attachment, the possible host range restrictions of BRS virus compared to HRS virus, and the roles of the individual viral antigens necessary to elicit a protective immune response in the natural host, which is something that cannot be done easily for HRS virus at present.

2.2. The G Protein

Previous work has shown that there is no cross reactivity between the attachment surface glycoproteins, G, of BRS virus and HRS virus, whereas there is cross antigenic reactivity between the other transmembrane glycoprotein, the fusion, F, protein and the major structural proteins, N, P, and M (Lerch et al., 1989, J. Virol. 63:833–840; Orville et al., 1987, J. Gen. Virol. 68:3125–3135). Available evidence indicates that BRS virus has a more narrow host restriction, infecting only cattle and bovine cells in culture, whereas HRS virus can infect a variety of cell types and experimental animals (Jacobs and Edington, 1975, Res. Vet. Sci. 18:299–306; Mohanty et al., 1976, J. Inf. Dis. 134:409–413; Paccaud and Jacquier, 1970, Arch. Gesamte Virusforsch 30:327–342). Since the G protein of HRS virus is the viral attachment protein (Levine et al., 1987, J. Gen. Virol.

68:2521–2524), this observation suggested that the differences in the BRS virus and HRS virus G proteins may be responsible for the differences in attachment and host range observed between BRS virus and HRS virus.

Based on sequence analysis of the HRS virus G mRNA, the G protein is proposed to have three domains; an internal or cytoplasmic domain, a transmembrane domain, and an external domain which comprises three quarters of the polypeptide (Satake et al., 1985, Nucl. Acids Res: 13:7795–7812; Wertz et al., 1985, Proc. Natl. Acad. Sci. U.S.A. 82:4075–4079). Evidence suggests that the respiratory syncytial virus G protein is oriented with its amino terminus internal, and its carboxy terminus external, to the virion (Olmsted et al., 1989, J. Viral. 13:7795–7812; Vijaya et al., 1988, Mol. Cell. Biol. 8:1709–1714; Wertz et al., 1985, Proc. Natl. Acad. Sci. U.S.A. 82:4075–4079). Unlike the other Paramyxovirus attachment proteins, the respiratory syncytial virus G protein lacks both neuraminidase and hemagglutinating activity (Gruber and Levine, 1983, J. Gen. Virol. 64:825–832; Richman et al., 1971, Appl. Microbiol. 21:1099). The mature G protein, found in virions and infected cells, has an estimated molecular weight of 80–90 kDa based on migration in SDS-polyacrylamide gels (Dubovi, 1982, J. Viol. 42:372–378; Gruber and Levine, 1983, J. Gen. Virol. 64:825–832; Lambert and Pons, 1983, Virology 130:204–214; Peeples and Levine, 1979, Viol. 95:137–145). In contrast, the G mRNA sequence predicts a protein with a molecular weight of 32 kDa (Satake et al., 1985, Nucl. Acids Res. 13:7795–7812; Wertz et al., 1985, Proc. Natl. Acad. Sci. U.S.A. 82:4075–4079), and when the G mRNA is translated in vitro it directs synthesis of a 36 kDa protein that is specifically immunoprecipitated by anti-G serum. It has been shown that there is N-linked and extensive O-linked glycosylation of the polypeptide backbone (Lambert, 1988, Virology 164:458–466; Wertz et al., 1989, J. Virol. 63:X). Experiments using glycosidases (inhibitors of sugar addition) and a cell line defective in O-linked glycosylation suggest that 55% of the molecular weight of the mature G protein is due to O-linked glycosylation, and 3% is due to N-linked glycosylation. However, these estimates are based on migration in SDS-polyacrylamide gels and are only approximate values. Consistent with the evidence for extensive O-linked glycosylation is a high content (30%) of threonine and serine residues in the predicted amino acid sequence of the G protein (Satake et al., 1985, Nucl. Acids Res. 13:7795–7812; Wertz et al., 1985, Proc. Natl. Acad. Sci. U.S.A. 82:4075–4079). Threonine and serine are amino acid residues that serve as sites for O-linked oligosaccharide attachment (Kornfield and Kornfield, 1980, in "The Biochemistry of Glycoproteins and Proteoglycans," Lenarz, ed., Plenum Press, N.Y. pp. 1–32) and in the HRS virus G protein 85% of the threonine and serine residues are in the extracellular domain (Wertz et al., 1985, Proc. Natl. Acad. Sci. U.S.A. 82:4075–4079). The high content of proline (10%), serine and threonine (30%) and the extensive O-linked glycosylation of the G protein are features similar to those of a group of cellular glycoproteins known as the mucinous proteins (Ibid.), but unusual among viral glycoproteins.

Isolates of HRS virus have been divided into two subgroups, A and B, based on the antigenic variation observed among G proteins using panels of monoclonal antibodies (Anderson et al., 1985, J. Inf. Dis. 151:626–633; Mufson et al., 1985, J. Gen. Virol. 66:2111–2124). However, a few monoclonal antibodies exist which recognize the G protein of both subgroups (Mufson et al., 1985, J. Gen. Virol. 66:2111–2124, orvell et al., 1987, J. Gen. Virol. 68:3125–3135). Sequence analysis of the G mRNA of HRS viruses from the two subgroups showed a 54% overall amino acid identity between the predicted G proteins, with 44% amino acid identity in the extracellular domain of the protein (Johnson et al., 1987 Proc. Natl. Acad. Sci. U.S.A. 84:5625–5629).

2.3. The F Protein

The mature BRS virus F protein consists of two disulfide linked polypeptides, $F_1$ and $F_2$ (Lerch et al., 1989, J. Virol. 63:833–840). There are differences in the electrophoretic mobility of the BRS virus and HRS virus F protein in SDS-polyacrylamide gels (Lerch et al., 1989, supra). Polyclonal and most monoclonal antibodies react to the F protein of both HRS virus and BRS virus (Stott et al., 1984; Orvell et al., 1987; Kennedy et al., 1988, J. Gen. Virol. 69:3023–3032; Lerch et al., 1989, supra).

The fusion protein, F, of paramyxoviruses causes fusion of the virus to cells and fusion of infected cells to surrounding cells. Structurally, the F proteins of the various paramyxoviruses are similar to one another. The F protein is synthesized as a precursor, $F_0$, that is proteolytically cleaved at an internal hydrophobic region to yield two polypeptides, $F_1$ and $F_2$, that are disulfide linked and form the active fusion protein. A carboxy terminal hydrophobic region in the $F_1$ polypeptide is thought to anchor the F protein in the membrane with its carboxy terminus internal to the cell and the amino terminus external. The F protein is N-glycosylated (see review, Morrison, 1988, Virus Research 10:113–136). The HRS virus F protein is a typical paramyxovirus fusion protein. Antibodies specific to the F protein will block the fusion of infected cells (Walsh and Hruska, 1983, J. Virol. 47:171–177; Wertz et al., 1987, J. Virol. 61:293–301) and also neutralize infectivity of the virus (Fernie and Gerin, 1982, Inf. Immun. 37:243–249; Walsh and Hruska, 1983, J. Virol. 47:171–177; Wertz et al., 1987, J. Virol. 61:293–301), but do not block attachment (Levine et al., 1987, J. Gen. Virol. 68:2521–2524). The F protein is synthesized as a polypeptide precursor $F_0$, that is cleaved into two polypeptides, $F_1$ and $F_2$. These two polypeptides are disulfide linked and N-glycosylated (Fernie and Gerin, 1982, Inf. Immun. 37:243–249; Gruber and Levine, 1983, J. Gen. Virol. 64:825–832; Lambert and Pons, 1983, Viral. 130:204–24).

2.4. Bovine Respiratory Syncytial Virus Vaccines

Bovine respiratory syncytial virus (BRS) vaccines have been developed comprising live or inactivated virus, or viral proteins. Frennet et al. (1984, Ann. Med. Vet. 128:375–383) reported that 81 percent of calves administered a combined live BRS virus and bovine viral diarrhea vaccine were protected against severe respiratory symptoms induced by field challenge. Stott et al. (1984, J. Hyg. 93:251–262) compared an inactivated BRS viral vaccine (consisting of glutaraldehyde-fixed bovine nasal mucosa cells persistently infected with BRS virus and emulsified with oil adjuvant) to two live vaccines, one directed toward BRS virus and the other toward HRS virus. Eleven out of twelve calves given the inactivated viral vaccine in the Stott study (supra) were completely protected against BRS viral challenge, but all control animals and those given the live vaccines became infected.

It is possible that live vaccines may exacerbate BRS viral infection. A severe outbreak of respiratory disease associated with BRS virus occurred shortly after calves were vaccinated with a modified live BRS virus (Kimman et al., 1989, Vet. Q. 11:250–253). Park et al. (1989, Res. Rep. Rural Dev. Adm. 31:24–29) reports the development of a binary ethylenimine (BEI)-inactivated BRS virus vaccine which was tested for its immunogenicity in guinea pigs and goats. Serum neutralizing antibody was detected 2 weeks following inoculation and antibodies increased following a booster vaccination at four weeks. In goats, a protective effect against BRS virus was observed when animals were challenged with virus 12 weeks following inoculation.

Trudel et al. (1989, Vaccine 7:12–16) studied the ability of immunostimulating complexes, made from the surface proteins of both human (Long) and bovine (A-51908) RS strains, adsorbed to the adjuvant Quil A, to induce neutralizing antibodies. Immunostimulating complexes prepared from bovine RS virus proteins were found to be significantly more efficient than their human counterpart in inducing neutralizing antibodies.

3. SUMMARY OF THE INVENTION

The present invention relates to recombinant DNA molecules which encode bovine respiratory syncytial (BRS) virus proteins, to BRS virus proteins and peptides and to recombinant BRS virus vaccines produced therefrom. It is based, in part, on the cloning of substantially full length cDNAs which encode the entire BRS virus G, F, and N proteins. Nucleotide sequences of the G, F, and N cDNAs have been determined, and are set forth in FIGS. 2A–C (G protein), FIGS. 9A–C (F protein), and FIGS. 17A and B (N protein).

According to particular embodiments of the invention, DNA encoding a BRS virus protein or peptide may be used to diagnose BRS virus infection, or, alternatively, may be inserted into an expression vector, including, but not limited to, vaccinia virus, as well as bacterial, yeast, insect, or other vertebrate vectors. These expression vectors may be utilized to produce the BRS virus protein or peptide in quantity; the resulting substantially pure viral peptide or protein may be incorporated into subunit vaccine formulations or may be used to generate monoclonal or polyclonal antibodies which may be utilized in diagnosis of BRS virus infection or passive immunization. In additional embodiments, BRS virus protein sequence provided by the invention may be used to produce synthetic peptides or proteins which may be utilized in subunit vaccines, or polyclonal or monoclonal antibody production. Alternatively, a nonpathogenic expression vector may itself be utilized as a recombinant virus vaccine.

4. DESCRIPTION OF THE FIGURES

FIG. 1. Sequencing strategy of G cDNAs of BRS virus. The scale at the bottom indicates the number of nucleotides from the 5' end of the BRS virus G mRNA. cDNA were inserted into M13 mp19 replicative form (RF) DNA and the nucleotide sequence determined by dideoxynucleotide sequencing using a M13 specific sequencing primer. The arrow indicates the portion of the G mRNA sequence determined by extension of a synthetic oligonucleotide primer on BRS virus mRNA. The sequence of the primer was complementary to bases 154–166 of the BRS virus G mRNA sequence. The cDNAs in clones G4, G10 and G33 were also excised using PstI and KpnI and inserted into M13 mp18 RF DNA for sequencing of the opposite end of the cDNA. The lines for each clone indicate the sequence of the mRNA determined from that clone. Only clones G10 and G33 were sequenced in their entirety. Clones G1, G7, G12, G5 and G3 were all less than 500 nucleotides in length and only partially sequenced for this reason.

FIGS. 2A–C. Alignment of the complete BRS virus G mRNA sequence with those of the HRS viruses A2 and 18537 G mRNAs. Alignment was done by the method of Needleman and Wunsch (1970, J. Mol. Biol. 48:443–453) comparing the BRS virus G sequence against the HRS virus A2 G sequence. Only nonidentical bases are shown for the G mRNA sequences of the HRS viruses A2 and 18537. Gaps, shown by the dotted lines, were used to maximize sequence identity of the HRS virus A2 G sequence as determined by Johnson et al. (1987, Proc. Natl. Acad. Sci. U.S.A. 84:5625–5629). The HRS virus consensus gene start and gene stop signals are overlined. The consensus initiation codon and the stop codon for the different viruses G mRNA are boxed. The dots above the sequences are spaced every ten nucleotides and the number of the last nucleotide on a line is indicated to the right of the sequence.

Figure 3A:
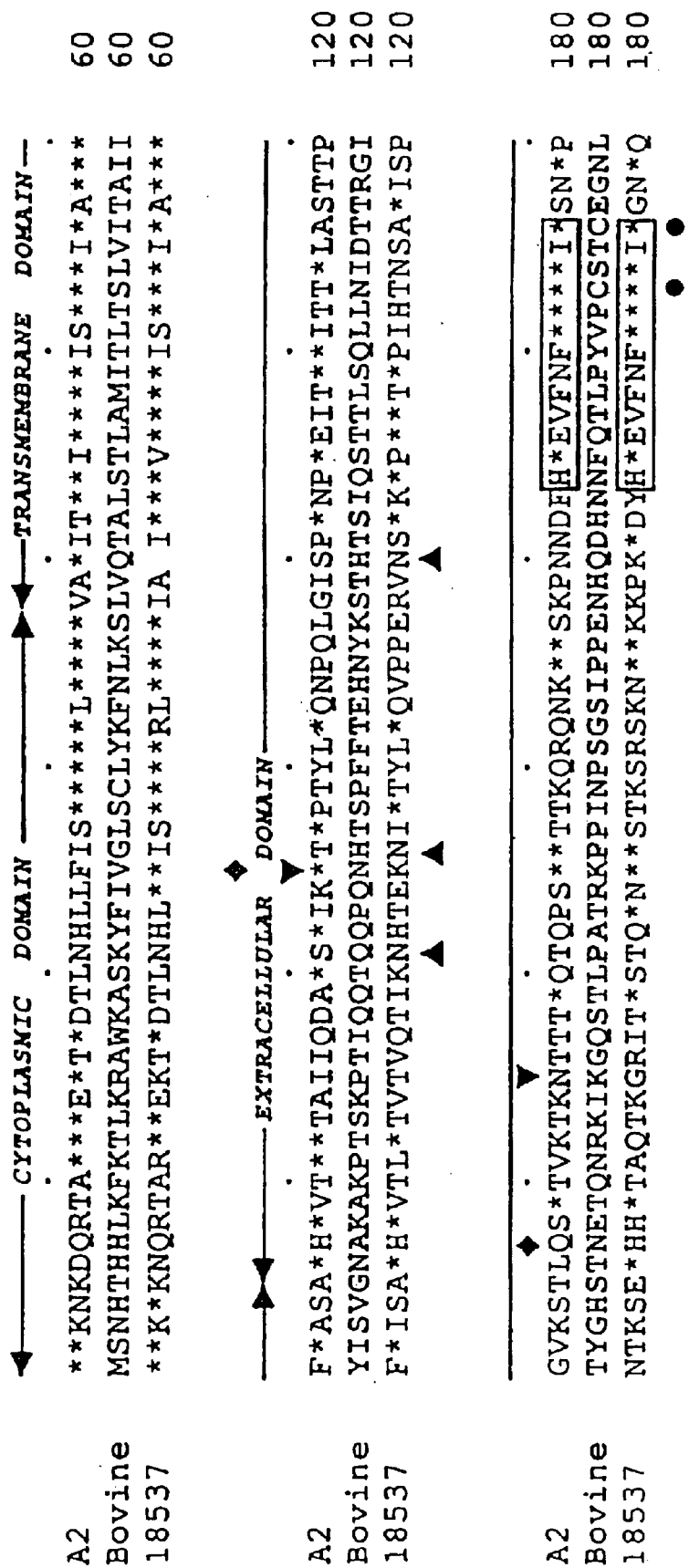

FIGS. 3A and B. Alignment of the predicted amino acid sequence of the BRS virus G protein and the G proteins of the HRS viruses A2 and 18537. Alignment was done by the method of Needleman and Wunsch (1970, J. Mol. Biol. 48:443–453). Identical amino acids for the HRS virus A2 and 18537 G proteins are indicated by an asterisk. The proposed domains are indicated above the sequence. Potential N-linked carbohydrate addition sites are indicated for the BRS virus G protein by black triangles above the sequences, for the HRS virus A2 G protein by black diamonds above the sequences, and for the HRS virus 18537 protein by black triangles below the sequences. The four conserved cysteine residues are indicated by the dark circles. The conserved thirteen amino acid region of the HRS virus A2 and 18537 G proteins is boxed. A gap in the HRS virus A2 G protein sequence compared to the HRS virus 18537 G protein sequence, as described by Johnson et al. (1987, Proc. Natl. Acad. Sci. U.S.A. 84:5625–5629) is shown by a dash. The dots above the sequences are spaced every ten amino acid residues and the number of the last amino acid residue on a line is indicated to the right of the sequence.

Figure 4:
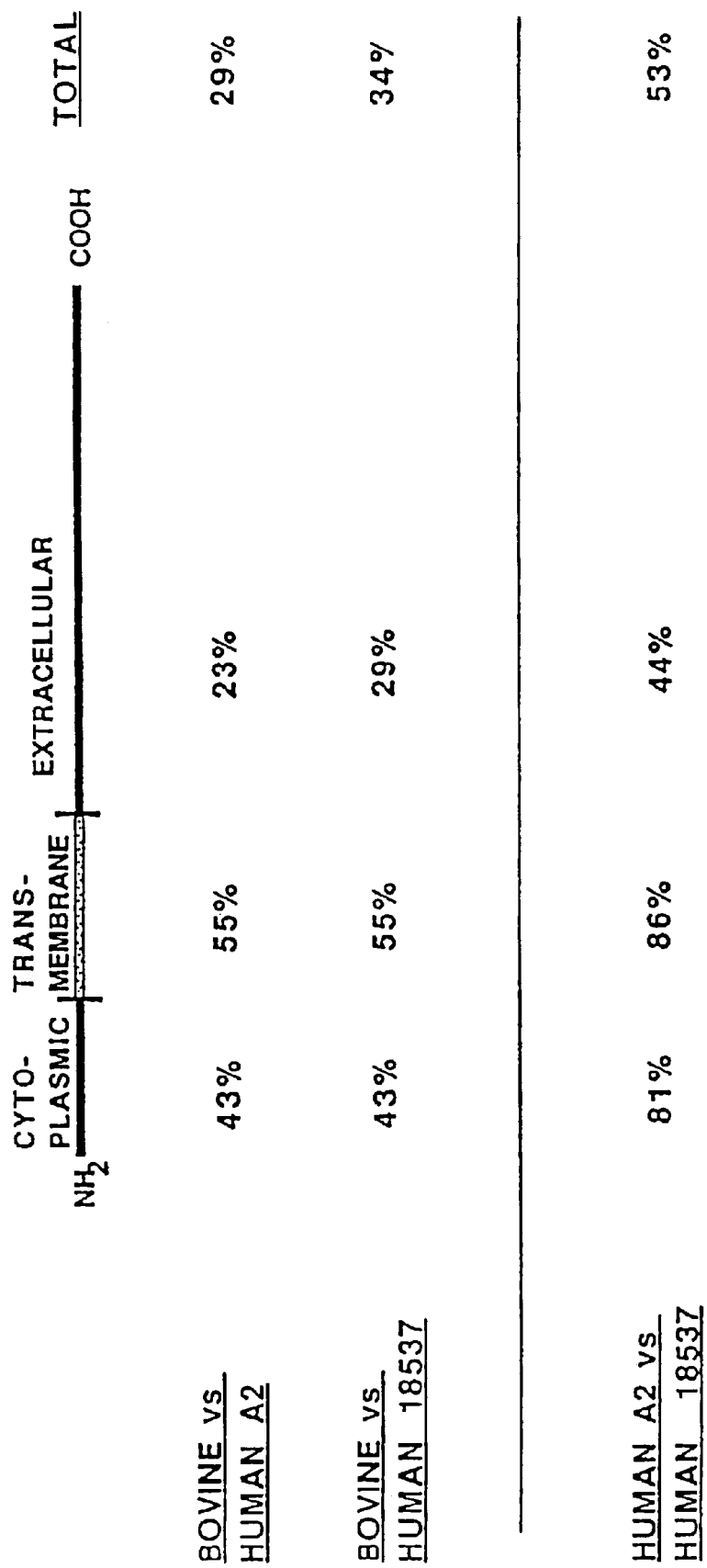

FIG. 4. Amino acid identity between the RS virus G proteins. The overall identity, and identity in the different proposed domains between the various G proteins is shown based on the alignment shown in FIG. 3.

Figure 5A:
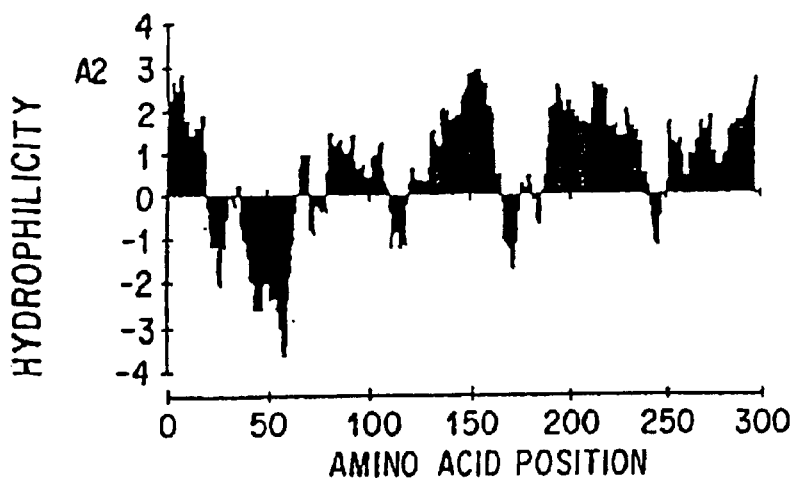
Figure 5B:
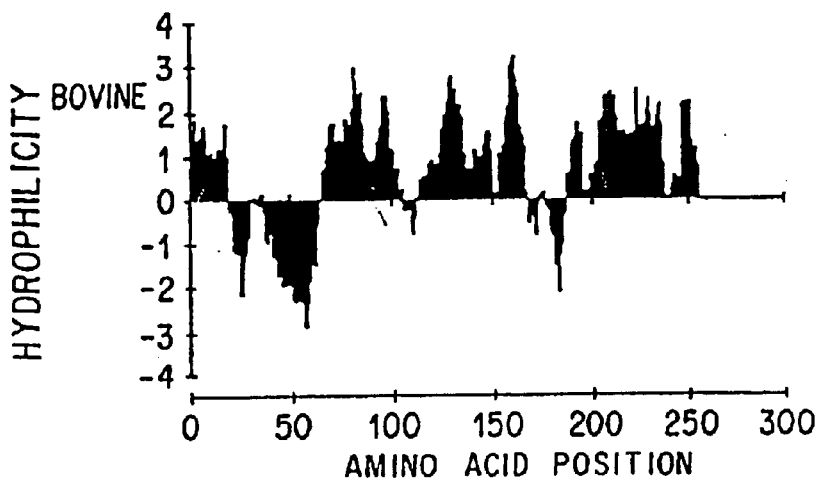
Figure 5C:
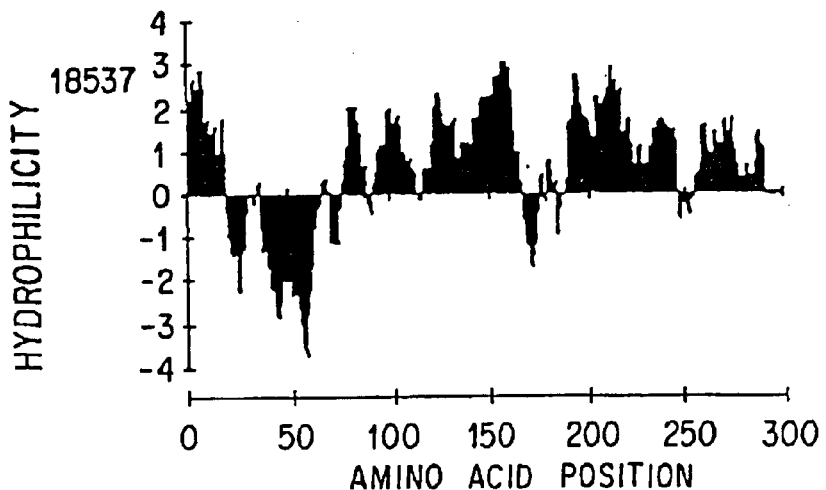

FIGS. 5A–C. Hydrophilicity plots for the G protein of BRS virus (FIG. 5B), and the HRS viruses A2 (FIG. 5A) and 18537 (FIG. 5C). The distribution of the hydrophilic and hydrophobic regions along the predicted amino acid sequence of the G proteins was determined using the algorithm of Kyte and Doolittle (1982, J. Mol. Biol. 157:105–132). The value for each amino acid was calculated over a window of nine amino acids. The bottom scale indicates the amino acid residue starting with the amino terminal methionine. Hydrophilic regions of the amino acid sequence are shown above the axis, and hydrophobic regions below the axis.

Figure 6:
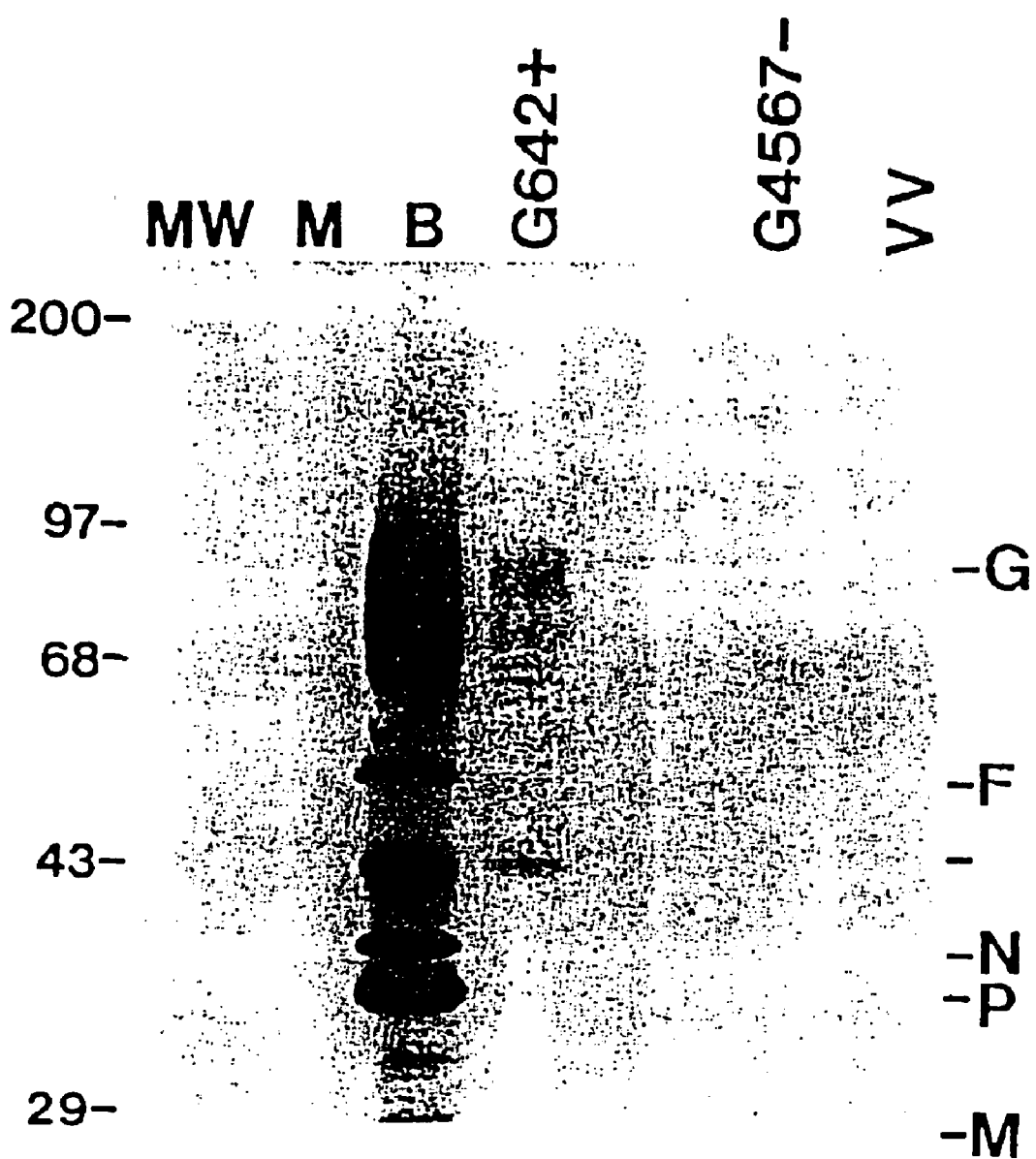

FIG. 6. Western blot analysis of BRS virus and recombinant vaccinia virus expressed G proteins. BT cells were infected with recombinant vaccinia viruses (moi=10), wild type vaccinia virus (moi=10) or BRS virus (moi=1). Proteins from BRS virus (lane B), wild type vaccinia virus (lane VV), recombinant vaccinia virus containing the BRS virus G gene in the forward (lane G642+) and reverse (lane G4567−) orientation, and mock (lane M) infected cells were harvested by lysing the cells at six hours postinfection for vaccinia virus infected cells, and 36 hours postinfection for BRS virus infected cells. The proteins were separated by electrophoresis in 10% polyacrylamide-SDS gel under non-reducing conditions, and analyzed by western blotting using anti-391-2 serum as a first antibody. Horseradish peroxidase-conjugated anti-bovine IgG was used to identify the bound first antibody. The BRS virus proteins are indicated. Prestained protein molecular weight markers are shown and labeled according to their molecular weight in kilodaltons.

FIG. 7. Surface immunofluorescence of recombinant vaccinia virus infected cells. HEp-2cells, grown on glass cover slips, were either mock (M) infected, infected with wild type vaccinia virus (VV; moi=10) or recombinant virus G642 (rVV; moi=10). At 24 hours postinfection, the live cells were stained with anti-391-2 serum, followed by fluorescein conjugated anti-bovine IgG (H+L). Phase contrast (left panels) and fluorescent (right panels) photographs are shown.

Figure 8:
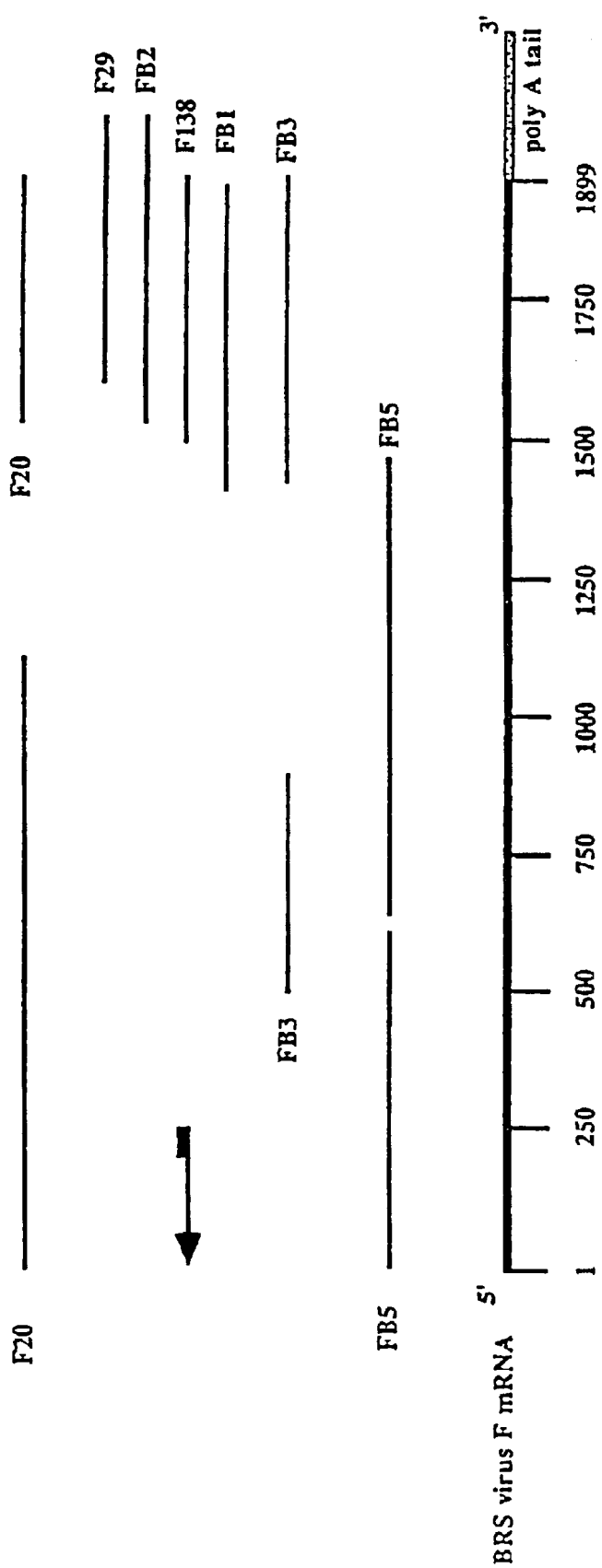

FIG. 8. Sequencing strategy of cDNAs of BRS virus F messenger RNA. The scale at the bottom indicates the number of nucleotides from the 5' end of the BRS virus F mRNA. cDNAs were inserted into M13 mp19 replicative form (RF) DNA and the nucleotide sequence was determined by dideoxynucleotide sequencing using a M13 specific sequencing primer. The lines for each clone indicate the portion of the mRNA sequence determined from that clone. The arrow indicates the area of the F mRNA sequence that was determined by extension of an oligonucleotide on BRS virus mRNA. The oligonucleotide was complementary to bases 267 to 284 of the BRS virus F mRNA. The cDNAs in clones F20, FB3, and FB5 were also excised using PstI and KpnI and inserted into M13 mp18 RF DNA for sequencing of the opposite end of the cDNA. Fragments of cDNAs in clones F20, FB5 and FB3 were generated by the use of the restriction enzymes EcoRI (FB3, FB5), or AlwNI (F20), PflMI (F20) and HpaI (F20) and EcoRV (F20) and subcloned back into M13 mp19, or mp18 RF DNA to determine the sequence in the internal areas of the F mRNA.

FIGS. 9A–C. Nucleotide sequence of the BRS virus F mRNA. The nucleotide sequence of the BRS virus F mRNA as determined from cDNA clones and primer extension on BRS virus mRNA is shown. The dots above the sequence are spaced every ten nucleotides and the number of the last base on a line is indicated to the right of the sequence. The predicted amino acid sequence of the major open reading frame is also shown. The number of the last codon starting on a line is indicated to the right of the amino acid sequence. The potential N-linked glycosylation sites are boxed. The amino terminal and carboxy terminal hydrophobic domains are underlined in black as is the hydrophobic region at the proposed amino terminus of the F1 polypeptide. The proposed cleavage sequence is underlined in gray.

Figure 10:
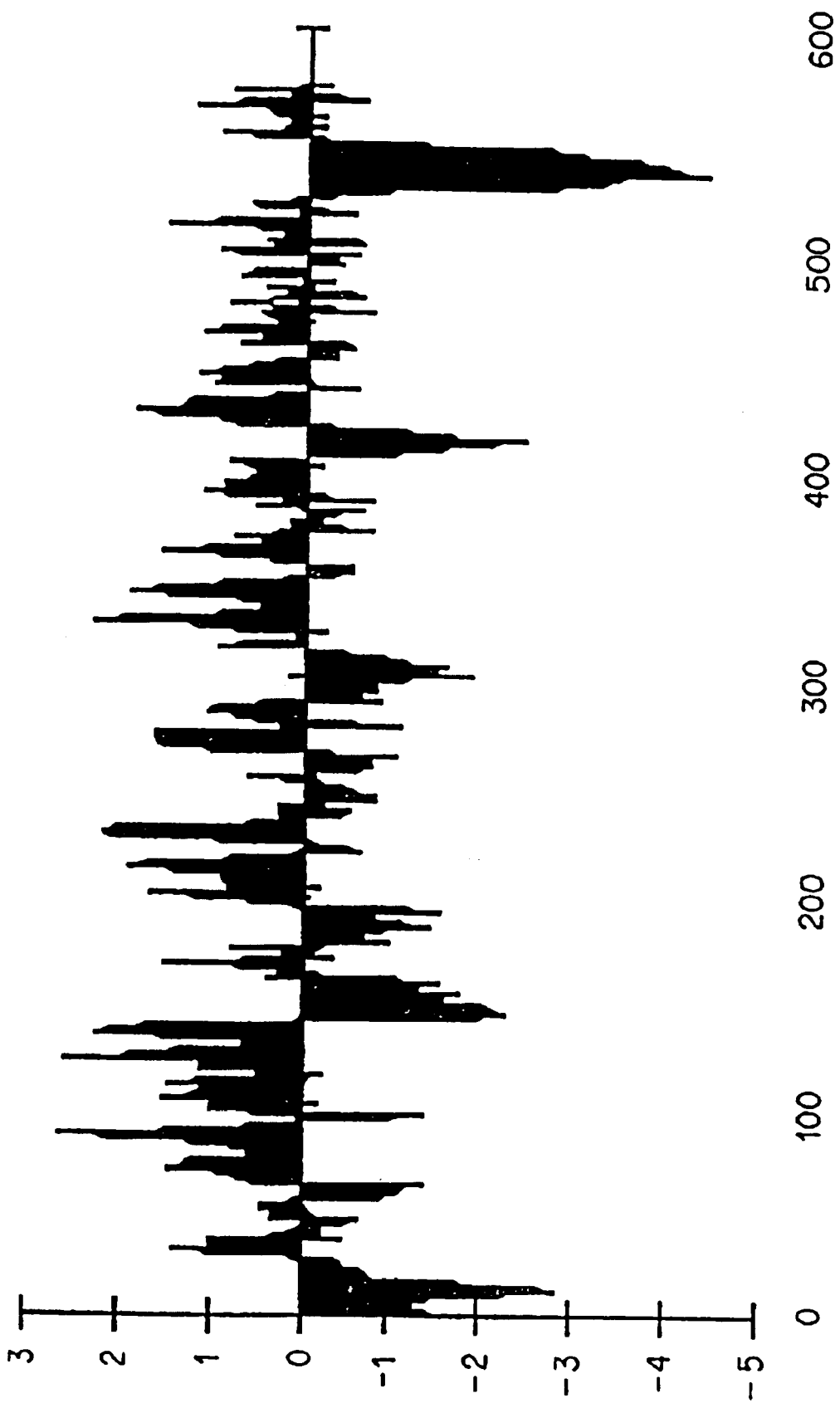

FIG. 10. Hydrophilicity plot for the F protein of BRS virus. The distribution of the hydrophilic and hydrophobic regions along the predicted amino acid sequence of the F protein was determined using the algorithm of Kyte and Doolittle (1982, J. Mol. Biol. 157:105–132). The value for each amino acid was calculated over a window of nine amino acids. The bottom scale indicates the amino acid residue starting with the amino terminal methionine. Hydrophilic regions of the amino acid sequence are shown above the axis, and hydrophobic regions below the axis.

FIGS. 11A–C. Alignment of the predicted amino acid sequences of the BRS virus F protein and the F proteins of HRS viruses A2, Long, RSS-2, and 18537. Alignment was done by the method of Needleman and Wunsch (1970, J. Mol. Biol. 48:443–453) comparing the BRS virus F protein against the F proteins of different HRS viruses. Only the non-identical amino acids are indicated for the HRS viruses F proteins. The dots below the sequence are spaced every ten amino acids and the number of the last residue on a line is indicated to the right of the sequence. The potential N-linked glycosylation sites of the proteins are boxed. Cysteine residues conserved between all five proteins are indicated by an open triangle. The amino terminal and carboxy terminal hydrophobic domains are underlined in black as is the hydrophobic region at the proposed amino terminus of the F1 polypeptide. The proposed cleavage sequence is underlined in gray.

Figure 12:
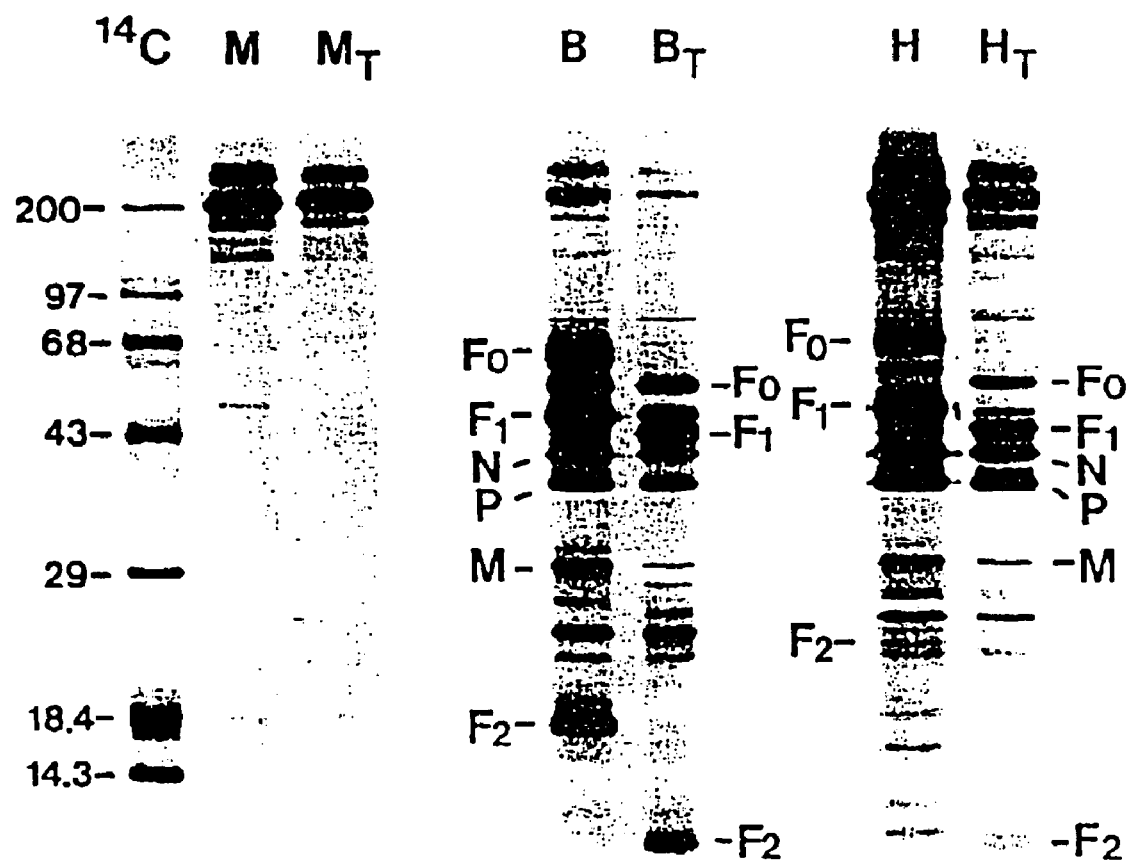

FIG. 12. Comparison of proteins from BRS virus and HRS virus infected cells synthesized in the presence and absence of tunicamycin. Proteins from BRS virus (B), HRS virus (H), or mock (M) infected cells were labeled by the incorporation of [$^{35}$S] methionine in the presence (lanes $B_T$, $H_T$, and $M_T$) or absence (lanes B, H and M) of tunicamycin. Virus specific proteins were immunoprecipitated using an anti-respiratory syncytial virus serum, and separated by electrophoresis on a 15% SDS-polyacrylamide gel. An autoradiograph of the gel is shown. All lanes are from the same gel with lanes H and HT from a longer exposure than the other lanes. [$^{14}$C]-labeled protein molecular weight markers are shown and labeled according to their molecular weight in kilodaltons.

Figure 13:
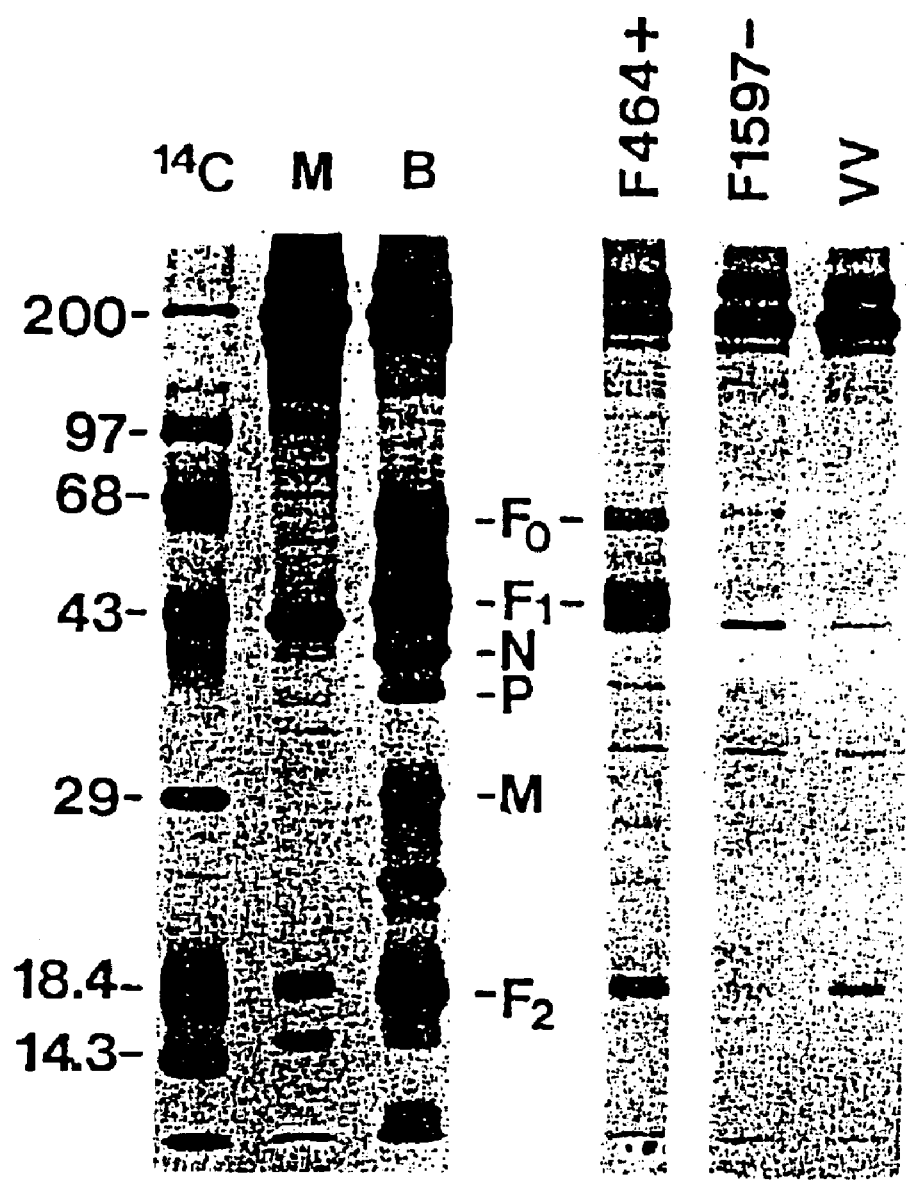

FIG. 13. Expression of the BRS virus F protein from recombinant vaccinia virus infected cells. BT cells were infected with recombinant vaccinia viruses (moi=10), wild type vaccinia virus (moi=10) or BRS virus (moi=1). Proteins from recombinant viruses containing the BRS virus F gene in the forward (lanes F464+) and reverse (F1597−) orientations and wild type vaccinia virus (VV) were radioactively labeled by the incorporation of [$^{35}$S] methionine from three to six hours postinfection. Proteins from BRS virus infected (lane B), and mock infected cells (lane M) which were also radioactively labeled by the incorporation of [$^{35}$S] methionine for three hours at 24 hours postinfection. The proteins were immunoprecipitated using the Wellcome anti-RS serum and compared by electrophoresis on a 15% polyacrylamide-SDS gel. Fluorography was done on the gel and an autoradiograph is shown. The BRS virus F, N, M and P proteins are indicated. [$^{14}$C]-labeled protein molecular weight markers are shown and labeled according to their molecular weight in kilodaltons.

Figure 14:
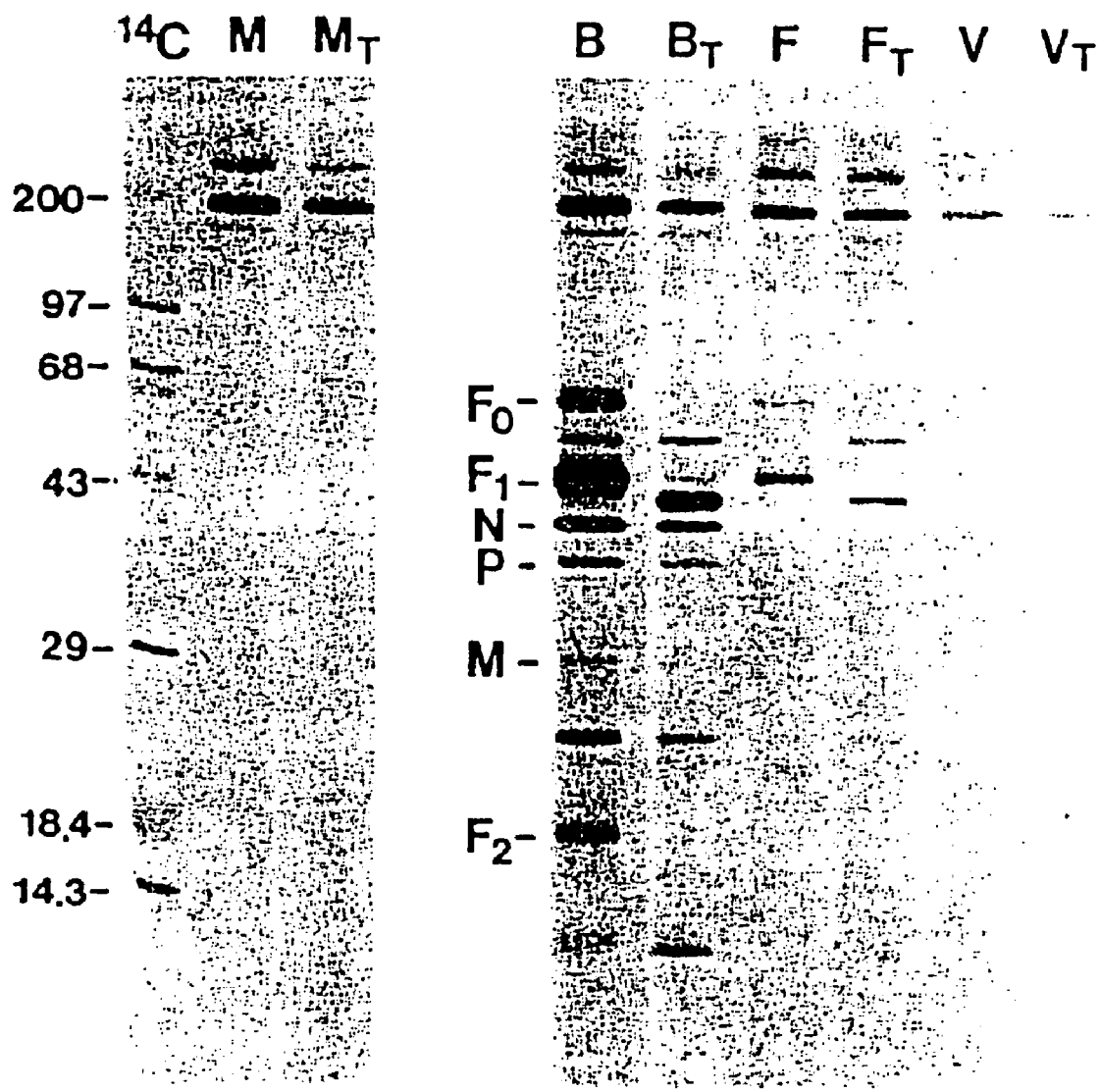

FIG. 14. Comparison of the BRS virus and recombinant vaccinia virus expressed F proteins synthesized in the presence of tunicamycin. BT cells were infected with recombinant vaccinia viruses (moi=10) wild type vaccinia virus (moi=10) or BRS virus (moi=1). Proteins from recombinant vaccinia viruses containing the BRS virus F gene in the forward orientation (F 464=F), wild type vaccinia virus (V), BRS virus infected (B) and mock infected cells (M) were radioactively labeled by the incorporation or [$^{35}$S]-methionine for three hours, at three hours postinfection for vaccinia infected cells and 24 hours postinfection for BRS virus infected cells, in the absence (lanes F, V, B, M) or presence (lanes $F_T$, $V_T$, $B_T$, $M_T$) of tunicamycin. The proteins were immunoprecipitated using the Wellcome anti-RS serum and compared by electrophoresis on a 15% polyacrylamide-SDS gel. Fluorography was done on the gel and an autoradiograph is shown. The BRS virus F, N, M and P proteins are indicated. [$^{14}$C]-labeled protein molecular weight markers are shown and labeled according to their molecular weight in kilodaltons.

Figure 15:
Figure 15:
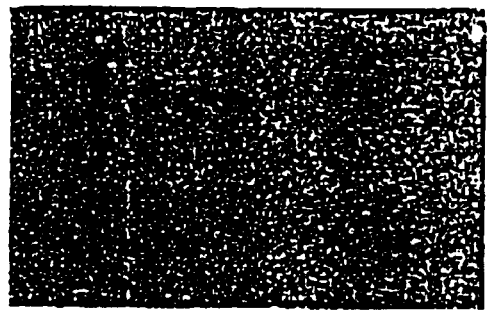
Figure 15:
Figure 15:
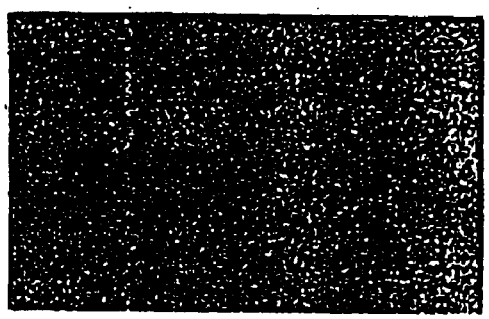
Figure 15:
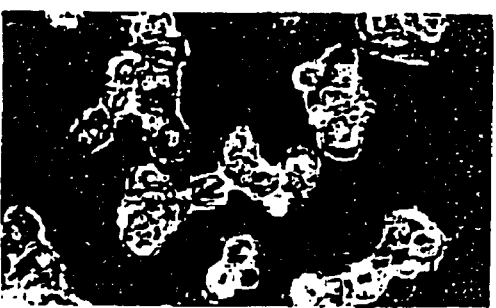
Figure 15:
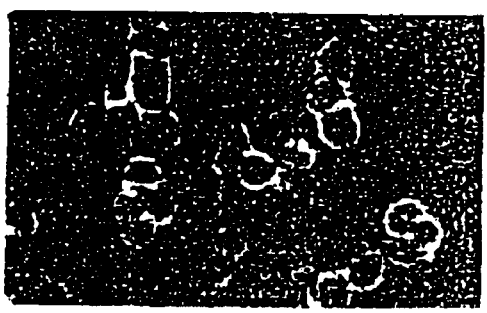

FIG. 15. Surface immunofluorescence of recombinant vaccinia virus infected HEp-2 cells. HEp-2 cells, grown on glass cover slips, were either mock (M) infected, infected with wild type vaccinia virus (VV; moi=10), recombinant virus F 464 (rVVf; moi=10). At 24 hours postinfection, the live cells were stained with anti-391-2 serum, followed by fluorescein conjugated anti-bovine IgG (H+L). Phase contrast (left panels) and fluorescent (right panels) photographs are shown.

Figure 16:
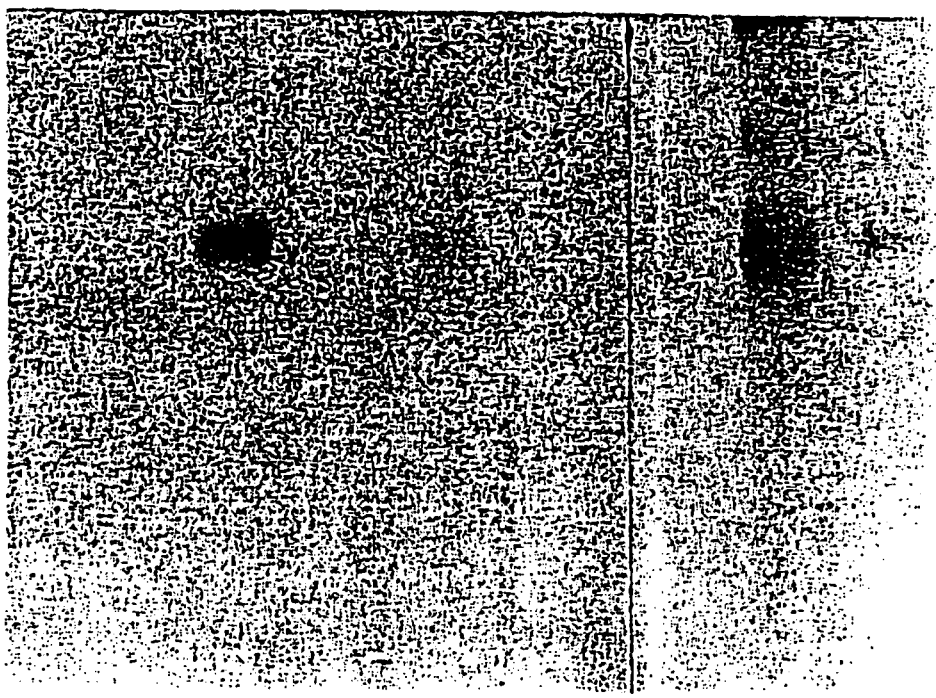

FIG. 16. Immunoprecipitation of $^3$H-glucosamine labeled proteins from mock (M) bovine RS virus (Bov) or human RS virus (Hu) infected BT cells. Panel A. Antisera specific for the human RS virus G protein was prepared by immunizing rabbits with a recombinant VV vector (vG301) expressing the HRS virus A2 G protein (Stott et al., 1986, J. Virol. 60:607–613) and used to immunoprecipitate the radiolabeled proteins from the mock, BRS virus (Bov) or HRS virus (Hu) infected cells. Panel B. Antisera specific for the bovine RS virus G protein was prepared by immunizing mice with a recombinant VV vector (vvG642) expressing the BRS virus G and used to immunoprecipitate proteins from the mock, BRS virus (Bov) or HRs virus (Hu) infected cells. Panel C. Total $^3$H-glucosamine labeled proteins present in cytoplasmic extracts of mock, BRS virus (Bov) or HRS virus (Hu) infected cells.

FIGS. 17A and B. Nucleotide sequence of the BRS virus N mRNA.

FIG. 18. Amino acid sequence of BRS virus N protein.

5. DETAILED DESCRIPTION OF THE INVENTION

The present invention relates to bovine respiratory syncytial virus nucleic acids and proteins. For purposes of clarity of disclosure, and not by way of limitation, the detailed description of the invention is divided into the following subsections:

(i) cloning bovine respiratory syncytial virus genes;

(ii) expression of bovine respiratory syncytial virus proteins;

(iii) the genes and proteins of the invention; and (iv) the utility of the invention.

5.1. Cloning Bovine Respiratory Syncytial Virus Genes

Bovine respiratory syncytial (BRS) virus genes, defined herein as nucleic acid sequences encoding BRS viral proteins, may be identified according to the invention by cloning cDNA transcripts of BRS virus mRNA and identifying clones containing full length BRS virus protein-encoding sequences, or, alternatively, by identifying BRS virus encoding nucleic acid sequences using probes derived from plasmids pRLG414-76-191, pRLF2012-76-192, or pRLNB3-76 or using oligonucleotide probes designed from the sequences presented in FIGS. 2A–C (SEQ ID No. 1), 9A–C (SEQ ID No. 3) or 17A and B (SEQ ID No. 5).

For example, and not by way of limitation, a cDNA containing the complete open reading frame of a BRS virus mRNA corresponding to a particular protein may be synthesized using BRS virus mRA template and a specific synthetic oligonucleotide for second strand synthesis. The nucleotide sequence for the oligonucleotide may be determined from sequence analysis of BRS viral mRNA. First strand synthesis may be performed as described in D'Alessio et al. (1987, Focus 9:1–4). Following synthesis, the RNA template may be digested with RNase A (at least about 1 µg/µl) for about 30 minutes at 37 degrees Centigrade. The resulting single-stranded cDNAs may then be isolated by phenol extraction and ethanol precipitation. The oligonucleotide used for second strand synthesis should preferably have a sequence specific for the 5' end of the viral mRNA of interest, and may also, preferably, contain a useful restriction endonuclease cleavage site to facilitate cloning. The single-stranded cDNAs may then be mixed with the oligonucleotide (at about 50 µg/ml), heated to 100 degrees C. for one minute and placed on ice. Reverse transcriptase may then be used to synthesize the second strand of the cDNAs in a reaction mixture which may comprise 50 mM Tris-HCl (pH 8.0), 50 mM KCl, 5 mM MgCl$_2$, 10 mM dithiothreitol, 1.6 mM dNTPs, and 100 U reverse transcriptase, incubated for about one hour at 50 degrees C. The cDNAs may then be separated from protein by phenol extraction, recovered by ethanol precipitation, and ends made blunt with T4 DNA polymerase. Blunt-ended cDNAs may then be digested with an appropriate restriction endonuclease (for example, which recognizes a cleavage site in the oligonucleotide primer but not within the protein-encoding sequence), separated from protein by phenol extraction, and then cloned into a suitable vector.

Alternatively, cDNAs generated from viral mRNA may be cloned into vectors, and clones carrying the nucleic acid sequences of interest may be generated using, as probes, oligonucleotides containing proteins of the nucleotide sequences presented in FIGS. 2A–C (SEQ ID No. 1) and 9A–C (SEQ ID No. 3) for the BRS virus G and F proteins, respectively. Viral cDNA libraries may be screened, for example, using the method set forth in Grunstein and Hogness (1975, Proc. Natl. Acad. Sci. U.S.A.). Retrieved clones may then be analyzed by restriction-fragment mapping and sequencing techniques (e.g., Sanger et al., 1979, Proc. Natl. Acad. Sci. U.S.A. 72:3918–3921) well known in the art. Alternatively, all or portions of the desired gene may be synthesized chemically based on the sequence presented in FIGS. 2A–C (SEQ ID No. 1) or 9A–C (SEQ ID No. 3).

In additional embodiments, primers derived from the nucleic acid molecules of the invention and/or nucleic acid sequences as set forth in FIGS. 2A–C (SEQ ID No. 1) or 9A–C, (SEQ ID No. 3) or nucleic acid sequences encoding amino acid sequences substantially as set forth in FIGS. 3A and B (SEQ ID No. 2) or 11A–C (SEQ ID No. 4), may be used in polymerase chain reaction (PCR); Saiki et al., 1985, Science 230:1350–1354) to produce nucleic acid molecules which encode BRS virus proteins or related peptides.

PCR requires sense strand as well as anti-sense strand primers. Accordingly, a degenerate oligonucleotide primer corresponding to one segment of BRS virus nucleic acid or amino acid sequence may be used as a primer for one DNA strand (e.g. the sense strand) and another degenerate oligonucleotide primer homologous to a second segment of BRS virus nucleic acid or amino acid sequence may be used as primer for the second DNA strand (e.g. the anti-sense strand). Preferably, these primers may be chosen based on a contiguous stretch of known amino acid sequence, so that the relevant DNA reaction product resulting from the use of these primers in PCR may be of a predictable size (i.e. the length of the product, in number of basepairs, should equal the sum of the lengths of the two primers plus three times the number of amino acid residues in the segment of protein bounded by the segments corresponding to the two primers). These primers may then be used in PCR with nucleic acid template which comprises BRS virus nucleic acid sequences, preferably cDNA prepared from BRS virus mRNA.

DNA reaction products may be cloned using any method known in the art. A large number of vector-host systems known in the art may be used. Possible vectors include, but are not limited to, cosmids, plasmids or modified viruses, but the vector system must be compatible with the host cell used. Such vectors include, but are not limited to, bacteriophages such as lambda derivatives, or plasmids such as pBR322, pUC, or Bluescript® (Stratagene) plasmid derivatives. Recombinant molecules can be introduced into host cells via transformation, transfection, infection, electroporation, etc.

The BRS virus gene may be inserted into a cloning vector which can be used to transform, transfect, or infect appropriate host cells so that many copies of the gene sequences are generated. This can be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Furthermore, primers used in PCR reactions may be engineered to comprise appropriate restriction endonuclease cleavage sites. In an alternative method, the cleaved vector and BRS viral gene may be modified by homopolymeric tailing. In specific embodiments, transformation of host cells with recombinant DNA molecules that incorporate an isolated BRS virus gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

5.2. Expression of Bovine Respiratory Syncytial Virus Proteins

The nucleotide sequence coding for a BRS virus protein, or a portion thereof, can be inserted into an appropriate expression vector, i.e., a vector which contains the necessary elements for the transcription and translation of the inserted protein-coding sequence. The necessary transcriptional and translation signals can also be supplied by the native BRS viral gene. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA, or cosmid DNA. The expression elements of these vectors vary in their strengths and specificities. Depending on the host-vector system utilized, any one of a number of suitable transcription and translation elements may be used.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinations (genetic recombination). Expression of nucleic acid sequence encoding BRS virus protein or peptide fragment may be regulated by a second nucleic acid sequence so that a BRS virus protein or peptide is expressed in a host transformed with the recombinant DNA molecule. For example, expression of BRS viral protein may be controlled by any promoter/enhancer element known in the art. Promoters which may be used to control BRS viral protein or peptide expression include, but are not limited to, the CMV promoter (Stephens and Cockett, 1989, Nucl. Acids Res. 17:7110), the SV40 early promoter region (Bernoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:144–1445), the regulatory sequences of the metallothionine gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25), see also "Useful proteins from recombinant bacteria" in Scientific American, 1980, 242:74–94; plant expression vectors comprising the nopaline synthetase promoter region (Herrera-Estrella et al., Nature 303:209–213) or the cauliflower mosaic virus 35S RNA promoter (Gardner, et al., 1981, Nucl. Acids Res. 9:2871), and the promoter for the photosynthetic enzyme ribulose biphosphate carboxylase (Herrera-Estrella et al., 1984, Nature 310:115–120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639–646: Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58); alpha 1-antitrypsin gene control region which is active in the liver (Kelsey et al, 1987, Genes and Devel. 1:161–171), beta-globin gene control region which is active in myeloid cells (Mogram et al., 1985, Nature 315:338–340; Kollias et al., 1986, Cell 46:89–94); myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Expression vectors containing BRS virus gene inserts can be identified by three general approaches: (a) DNA-DNA hybridization, (b) presence or absence of "marker" gene functions, and (c) expression of inserted sequences. In the first approach, the presence of a foreign gene inserted in an expression vector can be detected by DNA-DNA hybridization using probes comprising sequences that are homologous to an inserted BRS virus gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the BRS gene is inserted within the marker gene sequence of the vector, recombinants containing the BRS insert can be identified by the absence of the marker gene function. In the third approach, recombinant expression vectors can be identified by assaying the foreign gene product expressed by the recombinant.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus, in particular bovine adenovirus, as well as bovine herpes virus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered BRS virus protein may be controlled. Furthermore, different host cells have characteristic and specific mechanisms for the translational and post-translational processing and modification (e.g., glycosylation, cleavage) of proteins. Appropriate cell lines or host systems can be chosen to ensure the desired modification and processing of the foreign protein expressed. For example, expression in a bacterial system can be used to produce an unglycosylated core protein product. Expression in mammalian cells can be used to ensure "native" glycosylation of the heterologous BRS virus protein. Furthermore, different vector/host expression systems may effect processing reactions such as proteolytic cleavages to different extents.

Once a recombinant which expresses the BRS virus gene is identified, the gene product should be analyzed. This can be achieved by assays based on the physical or functional properties of the product.

Once the BRS virus protein or peptide is identified, it may be isolated and purified by standard methods including chromatography (e.g., ion exchange, affinity, and sizing column chromatography), centrifugation, differential solubility, or by any other standard technique for the purification of proteins.

In additional embodiments of the invention, BRS virus proteins or peptides may be produced by chemical synthesis using methods well known in the art. Such methods, are reviewed, for example, in Barany and Merrifield (1980, in "The Peptides," Vol. II, Gross and Meienhofer, eds., J. Academic Press, N.Y. pp. 1–284)

Additionally, recombinant viruses which infect but are nonpathogenic in cattle, including but not limited to vaccinia virus, bovine herpes virus and bovine adenovirus, may be engineered to express BRS virus proteins using suitable promoter elements. Such recombinant viruses may be used to infect cattle and thereby produce immunity to BRS virus. Additionally, recombinant viruses capable of expressing BRS virus protein, but which are potentially pathogenic, may be inactivated prior to administration as a component of a vaccine.

5.3. The Genes and Proteins of the Invention

Using the methods detailed supra and in Example Sections 6 and 7 infra, the following nucleic acid sequences were determined, and their corresponding amino acid sequences deduced. The BRS virus G protein cDNA sequence was determined, and the corresponding mRNA sequence is depicted in FIGS. 2A–C. BRS virus F protein cDNA sequence was determined, and the corresponding mRNA sequence is depicted in FIGS. 9A–C. BRS virus N protein cDNA sequence was determined, and the corresponding sequence is depicted in FIGS. 17A and B. Each of these sequences, or their functional equivalents, can be used in accordance with the invention. The invention is further directed to sequences and subsequences of BRS virus G, F or N protein encoding nucleic acids comprising at least ten nucleotides, such subsequences comprising hybridizable portions of the BRS virus G, F or N encoding nucleic acid sequence which have use, e.g., in nucleic acid hybridization assays, Southern and Northern blot analyses, etc. The invention also provides for BRS virus G, F or N proteins, fragments and derivatives thereof, according to the amino acid sequences set forth in FIGS. 3A and B (SEQ ID No. 2), 11A–C (SEQ ID No. 4) or 18 (SEQ ID No. 6) or their functional equivalents or as encoded by the following cDNA clones as deposited with the ATCC: pRLG414-76-191, pRLF2012-76-192, pRLNB3-76. The invention also provides fragments or derivatives of BRS virus G or F proteins which comprise antigenic determinant(s).

For example, the nucleic acid sequences depicted in FIGS. 2A–C (SEQ ID No. 1), 9A–C (SEQ ID No. 3) or 17A and B (SEQ ID No. 5) can be altered by substitutions, additions or deletions that provide for functionally equivalent molecules. Due to the degeneracy of nucleotide coding sequences, other DNA sequences which encode substantially the same amino acid sequence as depicted in FIGS. 3A and B, 11A–C or 18 may be used in the practice of the present invention. These include but are not limited to nucleotide sequences comprising all or portions of the nucleotide sequences encoding BRS virus G, F or N proteins depicted in FIGS. 2A–C (SEQ ID No. 1), 9A–C (SEQ ID No. 3) or 17A and B (SEQ ID No. 5) which are altered by the substitution of different codons that encode a functionally equivalent amino acid residue within the sequence, thus producing a silent change. Likewise, the BRS virus G, F or N proteins, or fragments or derivatives thereof, of the invention include, but are not limited to, those containing, as a primary amino acid sequence, all or part of the amino acid sequence substantially as depicted in FIGS. 3A and B (SEQ ID No. 2), 11A–C (SEQ ID No. 4) or 18 (SEQ ID No. 6) or as encoded by pRLG414-76-191, pRLF2012-76-192, or pRLNB3-76 including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the invention are BRS virus proteins or fragments or derivatives thereof which are differentially modified during or after translation, e.g., by glycosylation, proteolytic cleavage, linkage to an antibody molecule or other cellular ligand, etc.

In addition, the recombinant BRS virus G, F or N protein encoding nucleic acid sequences of the invention may be engineered so as to modify processing or expression of BRS virus protein. For example, and not by way of limitation, a signal sequence may be inserted upstream of BRS virus G, F or N protein encoding sequences to permit secretion of BRS virus G, F or N protein and thereby facilitate harvesting or bioavailability.

Additionally, a given BRS virus protein-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, et al., 1978, J. Biol. Chem. 253:6551), use of TABS® linkers (Pharmacia), etc.

5.4. The Utility of the Invention

5.4.1. Bovine Respiratory Syncytial Virus Vaccines

The present invention may be utilized to produce safe and effective BRS virus vaccines. According to the invention, the term vaccine is construed to refer to a preparation which elicits an immune response directed toward a component of the preparation. Advantages of the present invention include the capability of producing BRS virus proteins in quantity for use in vaccines or for the generation of antibodies to be used in passive immunization protocols as well as the ability to provide a recombinant virus vaccine which produces immunogenic BRS virus proteins but which is nonpathogenic. These alternatives circumvent the use of modified live BRS virus vaccines which may cause exacerbated symptoms in cattle previously exposed to BRS virus.

According to the invention, the BRS virus nucleic acid sequences may be inserted into an appropriate expression system such that a desired BRS virus protein is produced in quantity. In specific embodiments of the invention, BRS virus G, F or N proteins may be produced in quantity in this manner for use in subunit vaccines. In preferred specific embodiments of the invention, the BRS virus G, F or N protein may be expressed by recombinant vaccinia viruses, including, but not limited to, rVVF464 (F protein producing virus), or rVVG642 (G protein producing virus), harvested, and then administered as a protein subunit in a suitable pharmaceutical carrier.

Alternatively, recombinant virus, including, but not limited to, vaccinia virus, bovine herpes virus and bovine adenovirus and retroviruses which are nonpathogenic in cattle but which express BRS virus proteins, may be used to infect cattle and thereby produce immunity to BRS virus without associated disease. The production of the BRS G protein in recombinant virus vaccinated animals, or a portion or derivative thereof, may additionally prevent attachment of virus to cells, and thereby limit infection.

In further embodiments of the invention, BRS virus protein or peptide may be chemically synthesized for use in vaccines.

In vaccines which comprise peptide fragments of a BRS virus protein, it may be desirable to select peptides which are more likely to elicit an immune response. For example, the amino acid sequence of a BRS virus protein may be subjected to computer analysis to identify surface epitopes using a method such as, but not limited to, that described in Hopp and Woods (1981, Proc. Natl. Acad. Sci. U.S.A. 78:3824–3828), which has been successfully used to identify antigenic peptides of Hepatitis B surface antigen. It may also be desirable to modify the BRS virus peptides in order to increase their immunogenicity, for example, by chemically modifying the peptides or by linking the peptides to a carrier molecule.

The vaccines of the invention may be administered, in a suitable pharmaceutical carrier, by a variety of routes, including, but not limited to, nasally, orally, intramuscularly, subcutaneously, or intravenously and preferably intratracheally or by scarification. In preferred embodiments of the invention, between about $10^6$ and $10^8$ recombinant viruses may be administered in an inoculation. It may be desirable to administer subunit vaccines of the invention together with an adjuvant, for example, but not limited to, Freunds (complete or incomplete), mineral gels such as aluminum hydroxide, surface active substances such as lysolecithin, pluronic polyols, polyanions, peptides, oil emulsions, keyhole limpet hemocyanins, dinitrophenol, or Bacille calmette-Guerin (BCG) or *Corynebacterium parvum*. Multiple inoculations may be necessary in order to achieve protective and/or long-lasting immunity.

5.4.2. Antibodies Directed Toward Bovine Respiratory Syncytial Virus Proteins In additional embodiments, nucleic acid, protein or peptide molecules of the invention may be utilized to develop monoclonal or polyclonal antibodies directed toward BRS virus protein. For preparation of monoclonal antibodies directed toward a BRS virus protein, any technique which provides for the production of antibody molecules by continuous cell lines in culture may be used. For example, the hybridoma technique originally developed by Kohler and Milstein (1975, Nature 256:495–497) may be used.

A molecular clone of an antibody to a BRS virus protein may be prepared by known techniques. Recombinant DNA methodology (see e.g. Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule or antigen binding region thereof.

Antibody molecules may be purified by known techniques, e.g., immunoabsorption or immunoaffinity chromatography, chromatographic methods such as HPLC (high performance liquid chromatography), or a combination thereof, etc.

Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the 2 Fab or Fab fragments which can be generated by treating the antibody molecule with papain and a reducing agent.

5.4.3. Diagnostic Applications

The present invention, which relates to nucleic acids encoding BRS virus proteins and to proteins, peptide fragments, or derivatives produced therefrom, as well as antibodies directed against BRS virus proteins and peptides, may be utilized to diagnose BRS virus infection.

For example, the nucleic acid molecules of the invention may be utilized to detect the presence of BRS viral nucleic acid in BRS virus-infected animals by hybridization techniques, including Northern blot analysis, wherein a nucleic acid preparation obtained from an animal is exposed to a potentially complementary nucleic acid molecule of the invention under conditions which allow hybridization to occur and such that hybridization may be detected. For example, and not by way of limitation, total RNA may be prepared from swabs of nasal tissue, tracheal swabs, or isolates from any upper respiratory tract mucosal surface obtained from a cow potentially infected with BRS virus. The RNA may then be subjected to Northern blot analysis in which detectably labeled (e.g. radiolabeled) oligonucleotide probe derived from a BRS virus nucleic acid may be exposed to a Northern blot filter bearing the cow RNA under conditions permissive for hybridization; following hybridization, the filter may be washed and binding of probe to the filter may be visualized by autoradiography. Alternatively, if low levels of BRS virus are present in a diagnostic sample, it may be desirable to detect the presence of BRS virus nucleic acid using oligonucleotides of the invention in PCR reaction in order to amplify the amount of BRS virus nucleic acid present. In a preferred embodiment of the invention, viral RNA amplified from cultured cells may be analyzed for RS virus sequences by dot blot hybridization. The presence of BRS virus sequence not provided by the primer in the product of such a PCR reaction would be indicative of BRS virus infection.

In further embodiments, the BRS virus proteins and peptides of the invention may be used in the diagnosis of BRS virus infection. For example, and not by way of limitation, BRS virus proteins and peptides may be utilized in enzyme linked immunosorbent assay (ELISA), immunoprecipitation, rosetting or Western blot techniques to detect the presence of anti-BRS virus antibody. In preferred embodiments, a rise in the titer of anti-BRS virus antibodies may be indicative of active BRS virus infection. According to these embodiments, a serum sample may be exposed to BRS virus protein or peptide under conditions permissive for binding of antibody to protein or peptide and such that binding of antibody to protein or peptide may be detected. For example, and not by way of limitation, BRS virus protein or peptide may be immobilized on a solid surface, exposed to serum potentially comprising anti-BRS virus antibody (test serum) under conditions permissive for binding of antibody to protein or peptide, and then exposed to an agent which permits detection of binding of antibody to BRS virus protein or peptide, e.g. a detectably labeled anti-immunoglobulin antibody. Alternatively, BRS virus protein or peptide may be subjected to Western blot analysis, and then the Western blot may be exposed to the test serum, and binding of antibody to BRS virus protein or peptide may be detected as set forth above. In further, non-limiting embodiments of the invention, BRS virus protein or peptide may be adsorbed onto the surface of a red blood cell, and such antigen-coated red blood cells may be exposed to serum which potentially contains anti-BRS virus antibody. Rosette formation by serum of antigen coated red blood cells may be indicative of BRS virus exposure or active infection.

In additional embodiments of the invention, antibodies which recognize BRS virus proteins may be utilized in ELISA or Western blot techniques in order to detect the presence of BRS virus proteins, which would be indicative of active BRS virus infection.

6. EXAMPLE

Nucleotide Sequence of the Attachment Protein, G, of Bovine Respiratory Syncytial Virus and Expression from a Vaccinia Virus Vector

6. Materials and Methods

6.1.1. Virus and Cells

The growth and propagation of BRS virus isolate 391-2, wild type (Copenhagen strain) and recombinant vaccinia viruses (VV) bovine nasal turbinate (BT) cells, HEp-2 cells, and thymidine kinase negative (tk$^-$) 143B cells were as described in Hruby and Ball (1981, J. Virol. 40:456–464), Lerch et al., (1989, J. Virol. 63:833–840) and Stott et al. (1986, J. Virol. 60:607–613).

6.1.2. cDNA Synthesis, Molecular Cloning, and Identification of BRS Virus G Specific cDNA Clones cDNAs were synthesized using the strand replacement method of Gubler and Hoffman (1983, Gene 25:263–269) as described in D'Allesio, et al. (1987, Focus 9:1–4). T4 DNA polymerase (BRL) was used to make the ends of the cDNAs blunt (Maniatis et al., 1982, in "Molecular Cloning, a laboratory manual", Cold Spring Harbor Laboratory, Cold Spring Harbor, N.Y.). The cDNAs were ligated into M13mp19 replicative form (RF) DNA, which had been digested with SmaI and treated with calf intestinal alkaline phosphatase and transfected into competent E. coli DH5 αF' cells (Bethesda Research Laboratories; Hanahan, 1983, J. Mol. Biol. 166:557–580). M13mp19 phage containing BRS virus G specific inserts were identified by dot blot hybridization of phage DNA (Davis, et al., 1986, in "Basic Methods in Molecular Biology," Elsevier Science Publishing Co., Inc., N.Y., N.Y.) probed with a BRS virus G clone (Lerch et al., 1989, J. Virol. 63:833–840) that had been labeled by nick translation (Rigby, et al., 1977, J. Mol. Biol. 113:237–251). Growth and manipulations of M13mp19 and recombinant phage were as described by Messing (1983, Methods Enzymol. 101:20–78).

6.1.3. Nucleotide Sequencing and Primer Extension on RNA

Dideoxynucleotide sequencing using the Klenow fragment of E. coli DNA polymerase I (Pharmacia) or a modified T7 DNA polymerase (Sequenase, U.S. Biochemicals) was done essentially as described in Lim and Pene (1988, Gene Anal. Tech. 5:32–39) and Tabor and Richardson (1987, Proc. Natl. Acad. Sci. U.S.A. 84:4746–4771) using an M13 sequencing primer (New England Biolabs). Extension of a synthetic DNA primer, complementary to bases 154 to 166 of the BRS virus G mRNA, on BRS virus mRNA template using Avian myeloblastosis virus (AMV) reverse transcriptase (Molecular Genetic Resources) was done to determine the 5' sequence of the BRS virus G mRNA (Air, 1979, Virol. 97:468–472). BRS virus mRNA used as template in the primer extension on RNA was harvested as described for mRNA used for cDNA synthesis (Lerch et al., 1989, J. Virol. 63:833–840). Nucleotide sequencing and primer extension were done using [α-$^{35}$S] dATP (Amersham) and polyacrylamide-urea gradient gel electrophoresis as described by Biggin et al. (1983, Proc. Natl. Acad. Sci. U.S.A. 80:3963–3965). The nucleotide sequence was analyzed using the University of Wisconsin Genetics Computer Group software package (Devereux, et al., 1984, Nucleic Acids Res. 12:387–395).

6.1.4. Synthesis and Cloning of Complete cDNAs to the BRS Virus G mRNA

A cDNA containing the complete open reading frame of the BRS virus G mRA was synthesized using a specific synthetic oligonucleotide for second strand synthesis. The nucleotide sequence for the oligonucleotide was determined from sequence analysis of BRS virus mRNAs. First strand synthesis occurred as described in D'Alessio et al. (1987, Focus 9:1–4). Following synthesis, the RNA template was digested with RNase A (1 .mu.g/.mu.1) for thirty minutes at 37 degrees Centigrade (C.). The resulting single stranded cDNAs were isolated by phenol extraction and ethanol precipitation. The oligonucleotide used for second strand synthesis had the sequence 5'CACGGATCCACAAGTAT-GTCCAACC 3' (SEQ ID No. 7) with the 5' first nine bases of the oligonucleotide containing a BamHI restriction enzyme site in the gene. The single-stranded cDNAs were mixed with the oligonucleotides at a concentration of about 50 .mu.g/ml, heated to 100 degrees C. for one minute and placed on ice. AMV reverse transcriptase was used to synthesize the second strand of the cDNAs in a reaction comprising 50 mM Tris-HCl (pH8.0), 50 mM KCl, 5 mM $MgCl_2$, 10 mM dithiothreitol, 1.6 mM dNTPs, and 100 U AMV reverse transcriptase that was incubated for one hour at 50.degree. C. The cDNAs were separated from protein by phenol extraction, recovered by ethanol precipitation, and ends made blunt with T4 DNA polymerase. Blunt-ended cDNAs were then digested with the restriction enzyme BamHI (Bethesda Research Laboratories) and separated from protein by phenol extraction. M13mp18 RF DNA, that was digested with BamHI and SmaI and treated with calf intestinal phosphatase, was mixed in solution with the cDNAs and recovered by ethanol precipitation. The cDNAs and vector were ligated and transfected into competent DH5.alpha.F' cells (Bethesda Research Laboratories) as described in Hanahan (1983, J. Mol. Biol. 166:557–580).

6.1.5. Construction and Isolation of Recombinant Vaccinia Virus Vectors

A complete cDNA clone, G4, corresponding to the BRS virus G mRNA was subcloned into a recombinant plasmid, pIB176-192, by digestion with BamHI and KpnI, treatment with T4 DNA polymerase to make the ends of the cDNA blunt, and ligation into the unique SmaI site of pIB176-192. The plasmid pIB176-192 is similar to recombination plasmids described in Ball, et al, (1986, Proc. Natl. Acad. Sci. USA 83:246–250). pIB176–192 contains base pairs (bp) 1 to 1710 of the HindIII J fragment of vaccinia virus inserted between the HindIII and SmaI sites of pIB176 (International Biotechnology Inc.). Inserted into the EcoRI site (bp 670 of the HindIII J fragment) of the vaccinia virus thymidine kinase (tk) gene (bp 502 to 1070 of the HindIII J fragment; Weir and Moss, 1983, J. Virol. 46: 530–537) is a 280 bp fragment of DNA that contains the 7.5K promoter of vaccinia virus. The orientation of this promoter fragment was such that it directed transcription from right to left on the conventional vaccinia virus map, opposite to the direction of transcription of the vaccinia virus tk gene. The unique SmaI site in pIB176-192 is downstream from the major transcriptional start site of the 7.5K promoter.

The isolation of recombinant vaccinia viruses containing the BRS virus G mRNA sequence was as described in Stott, et al. (1986, J. Virol. 60:607–613) except that the recombinant viruses were identified using the blot procedure of Lavi and Ektin (1981, Carcinogenesis 2:417–423).

6.1.6. Characterization of Recombinant Vaccinia Virus Vectors

Vaccinia virus core DNA from wild type and recombinant viruses was prepared for Southern blot analysis as described by Esposito et al. (1981, J. Virol. Methods 2:175–179). Restriction enzyme digestion, Southern blot analysis, and radioactive labeling of DNA by nick translation were performed using standard techniques (Maniatis et al., 1982, in "Molecular Cloning: a laboratory manual," Cold Spring Harbor Laboratory, Cold Spring Harbor, N.Y.; Rigby , et al., 1977, J. Mol. Biol. 113:237–251). Metabolic labeling of proteins from BRS virus and wild type and recombinant vaccinia virus infected cells was as described in Lerch et al. (1989, J. Virol. 63:833–840) except that proteins in vaccinia virus infected cells were labeled for three hours starting at three hours postinfection. SDS-polyacrylamide gel electrophoresis of proteins was done using standard procedures. For western blot analysis, proteins from infected and uninfected cells were harvested as described in Lerch et al. (1989, J. Virol. 63:833–840) at thirty hours postinfection for BRS virus infected BT cells, and six hours postinfection for vaccinia virus infected BT cells. Anti-BRS virus 391-2 serum (ibid) was used in the western blot analysis. Immunofluorescence was done on HEp-2 grown on glass cover slips. [Hep-2] cells were infected with wild type or recombinant vaccinia viruses (multiplicity of infection (moi)=10). At 48 hours postinfection, the cells were stained for surface immunofluorescence using anti-BRS virus 391-2 serum as a first antibody followed by fluorescein conjugated anti-bovine IgG (H+L). Fluorescence was observed through a fluorescence microscope available through Nikon.

6.2. Results

6.2.1. Nucleic Acid Sequence and Comparison

In order to determine the sequence of the BRS virus G mRNA and deduce the amino acid sequence, cDNAs to the BRS virus G mRNA were generated, and the nucleotide sequence was determined from nine cDNA clones. The nine clones were derived independently from four separate cDNA synthesis reactions. Direct sequencing of the 5' end of G mRNA by primer extension of a synthetic DNA primer on BRS virus mRNA was also performed. The areas of the BRS virus G mRNA sequence determined from the different clones and from primer extension are shown in FIG. 1. Clone G4 is a full length BRS virus G clone synthesized using an oligonucleotide primer specific for second strand synthesis. Three independent clones, G4 (bases 8–838), G10 (bases 19–828) and G33 (bases 23–808), were excised with PstI an KpnI, and subcloned into M13mp18 RF DNA to allow for sequencing from the opposite end of the cDNA. Clones G10 and G33 were sequenced in their entirety. Clones G1, G7, G12, G5, and G3 were all less than 500 nucleotides in length and only partially sequenced for this reason.

The BRS virus G protein mRNA was found to be about 838 nucleotides in length excluding the polyadenylate tail (FIGS. 2A–C) (SEQ ID No. 1). The BRS virus G mRNA sequence was compared to the published nucleotide sequences of the G protein mRNAs of HRS viruses A2 and 18537, a subgroup A virus and a subgroup B virus, respectively (FIGS. 2A–C) (Johnson et al., 1987, Proc. Natl. Acad. Sci. U.S.A. 84:5625–5629; Wertz et al., 1985, Proc. Natl. Acad. Sci. U.S.A. 82: 4075–4079). The BRS virus G mRNA was shorter than the HRS virus A2 and 18537 G mRNAs by 81 and 84 bases, respectively. There were some conserved features in common between the BRS virus G mRNA and the HRS virus G mRNAs. With the exception of the first nucleotide, the BRS virus G mRNA had the conserved gene start signal 5'GGGGCAAAU . . . 3'. Collins, et al., (1986, Proc. Natl. Acad. Sci. USA 83:4594–4598) found at the 5' end of all HRS virus mRNAs. The 3' end of the BRS virus G mRNA also conformed to one of the two concensus gene end sequences 5' . . . $AGU_{-}U^{A}AU_{-}U^{A}$ Upoly A3' found at the 3' end of all HRS virus genes (Collins, et al., 1986, Proc. Natl. Acad. Sci. USA 83:4594–4598). The position of the initiation codon, nucleotides 16–18, for the major open reading frame of the BRS virus G mRNA was identical to the position of the initiation codons of the G mRNAs of HRS viruses (Johnson et al., 1987, Proc. Natl. Acad. Sci. U.S.A. 84:5625–5629; Satake, et al., 1985, Nucleic Acids Res. 13:7795–7812; Wertz et al., 1985, Proc. Natl. Acad. Sci. U.S.A. 82:4075–4079). The noncoding region at the 3' end of the BRS virus mRNA, however, was 42 bases long compared to six bases for the HRS virus A2G mRNA and 27 bases for the HRS virus 18537 G mRNA (Johnson et al., 1987, Proc. Natl. Acad. Sci. U.S.A. 84:5625–5629; Satake, et al., 1985, Nucleic Acids Res. 13:7795–7812; Wertz et al., 1985, Proc. Natl. Acad. Sci. U.S.A. 82:4075–4079). This resulted in the termination codon for the BRS virus G protein occurring 119 bases prior to the termination codon for the G protein of HRS virus A2, and 98 bases prior to the termination codon in the 18537 G mRNA. One clone, G4, was missing bases 812, 819 and 824, all of which were after the termination codon in the 3' noncoding region. The BRS virus G mRNA lacked an upstream ATG found in the HRS virus G mRNAs (Johnson et al., 1987, Proc. Natl. Acad. Sci. U.S.A. 84:5625–5629; Satake, et al., 1985, Nucleic Acids Res. 13:7795–7812; Wertz et. al., 1985, Proc. Natl. Acad. Sci. U.S.A. 82:4075–4079).

The BRS virus G mRNA shared 51.7% sequence identity with the HRS virus A2 G mRNA and 50.8% with the HRS virus 18537 G mRNA when the BRS virus G mRNA was aligned with the HRS virus A2 G mRNA. The HRS virus A2 and 18537 G mRNAs share 67.4% sequence identity (Johnson et al., 1987, Proc. natl. Acad. Sci. U.S.A. 84: 5625–5629). A slightly different alignment occurs when the BRS virus G mRNA is aligned with the HRS virus 18537 G mRNA, but resulted in a change of less than 1% in sequence identity between the G mRNA of BRS virus and the G mRNA of either HRS virus A2 or 18537 viruses. Computer analysis was used to determine if an internal deletion would result in a better alignment, but one was not found.

6.2.2. Amino Acid Sequence and Comparison

The BRS virus G mRNA had a major open reading frame which predicted a polypeptide of 257 amino acids. The predicted molecular weight of this polypeptide was 28.6 kD. The deduced amino acid sequence of the BRS virus G protein is shown (FIGS. 3A and B) (SEQ ID No. 2) and compared with the published amino acid sequences of the HRS virus A2 and 18537 G proteins (Johnson et al., 1987, Proc. Natl. Acad. Sci. U.S.A. 84:5625–5629; Wertz et al., 1985, Proc. Natl. Acad. Sci. U.S.A. 82:4075–4079). The BRS virus G protein was similar in overall amino acid composition to the HRS virus G proteins, with a high content of threonine and serine residues, 25.7%, compared to that observed for the G proteins of the HRS viruses 18537 (28.4%) and A2 (30.6%). Serine and threonine residues are potential sites for the addition of O-linked carbohydrate side chains. Out of 66 threonine and serine residues in the BRS virus protein, 52 (79%) of these are in the proposed extracellular domain. The position of only nine threonine residues (amino acids 12, 52, 72, 92, 129, 139, 199, 210, 211, 235) and eight (8) serine residues (amino acids 2, 28, 37, 44, 53, 102, 109, 174) were conserved between predicted amino acid sequences of all the G proteins examined to date (FIGS. 3A and B) (SEQ D No. 2). In addition to the potential O-linked carbohydrate addition sites, there were four sites for potential N-linked carbohydrate addition in the BRS virus G protein. The position of none of the potential N-linked addition sites was conserved between BRS virus and the subtype B HRS virus; two of the four potential sites were the same in HRS virus A2 and BRS virus G proteins. The BRS virus G protein had a high proline content, 7.8%, similar to that observed for the G proteins of the HRS viruses A2 (10%) and 18537 (8.6%) (Johnson et al., 1987, Proc. Natl. Acad. Sci. U.S.A. 84:5625–5629; Satake, et al., 1985, Nucleic Acids Res. 13:7795–7812; Wertz et al., 1985, Proc. Natl. Acad. Sci. U.S.A. 82:4075–4079). Six proline residues were conserved among all RS virus G proteins sequenced to date. These proline residues were amino acids 146, 155, 156, 172, 194, and 206 (FIGS. 3A and B) (SEQ ID No. 2). There were four cysteine residues in the proposed extracellular domain of the BRS virus G protein. These four residues were exactly conserved in position, relative to the amino terminus of the protein, with the four cysteine residues conserved among the HRS virus A2, Long and 18537 (FIGS. 3A and B) (SEQ ID No. 2) (Johnson et al., 1987, Proc. Natl. Acad. Sci. U.S.A. 84:5625–5629; Satake, et al., 1985, Nucleic Acids Res. 13:7795–7812; Wertz et al., 1985, Proc. Natl. Acad. Sci. U.S.A. 82:4075–4079). In addition, the G proteins of BRS virus, HRS virus A2, and HRS virus 18537 all shared a cysteine residue in the proposed cytoplasmic domain (FIGS. 3A and B) (SEQ ID No. 2). However, this cysteine residue is not present in the HRS virus Long G protein.

The BRS virus G protein had a high proline content, 7.8%, similar to that observed for the G proteins of the HRS viruses A2 (10%) and 18537 (8.6%) (Johnson et al., 1987, Proc. Natl. Acad. Sci. U.S.A. 84:5625–5629; Satake, et al., 1985, Nucleic Acids Res. 13:7795–7812; Wertz et al., 1985, Proc. Natl. Acad. Sci. U.S.A. 82:4075–4079). Six proline residues were conserved among all RS virus G proteins sequenced to date. These proline residues were amino acids 146, 155, 156, 172, 194, and 206 (FIGS. 3A and B).

There were four cysteine residues in the proposed extracellular domain of the BRS virus G protein. These four residues were exactly conserved in position, relative to the amino terminus of the protein, with the four cysteine residues conserved among the HRS virus A2, Long and 18537 (FIGS. 3A and B) (Johnson et al., 1987, Proc. Natl. Acad. Sci. U.S.A. 84:5625–5629; Satake, et al., 1985, Nucleic Acids Res. 13:7795–7812; Wertz et al., 1985, Proc. Natl. Acad. Sci. U.S.A. 82:4075–4079). In addition, the G proteins of BRS virus, HRS virus A2, and HRS virus 18537 all shared a cysteine residue in the proposed cytoplasmic domain (FIGS. 3A and B). However, this cysteine residue is not present in the HRS virus Long G protein.

While the cysteine residues were conserved in the BRS virus G protein, a thirteen amino acid region reported previously to be exactly conserved in the E proteins of subgroups A and B HRS viruses was not conserved in the BRS virus G protein. Only six of the thirteen amino acids in this region of the BRS virus G protein were conserved, and two of these six were the cysteine residues (FIGS. 3A and B) (SEQ ID No. 2).

The amino acid identity among the BRS virus G protein and the HRS virus proteins was significantly lower than the amino acid identity observed between the G proteins of the HRS virus subgroup A and B (FIG. 4). The overall amino acid identity between the HRS virus A2 and 18357 G proteins is 53%. The BRS virus G protein shared only 29% amino acid identity with the HRS virus A2 G protein and 30% amino acid identity with the HRS virus 18537 G protein. Comparison of amino acid identity within each of the three postulated domains of the G proteins showed distinct differences in the levels of identity in the three domains. The identity between the proposed extracellular domain of the BRS virus and HRS virus G proteins was significantly lower than the overall amino acid identity, and lower than the identity between extracellular domains of the two HRS virus G proteins (FIG. 4). The proposed cytoplasmic and transmembrane domains of the BRS virus G protein were more conserved than the extracellular domain, with 43% and 55% amino acid identity, respectively, observed among the corresponding domains of either HRS virus G protein (FIG. 4).

Although the overall identity of the BRS virus G protein to either HRS G protein was lower than that between HRS virus G proteins, there were similarities in the hydropathy profiles of the different G proteins (FIGS. 5A–C) (Johnson et al., 1987, Proc. Natl. Acad. Sci. U.S.A. 84:5625–5629; Satake, et al., 1985, Nucleic Acids Res. 13:7795–7812; Wertz et al., 1985, Proc. Natl. Acad. Sci. U.S.A. 82:4075–4079). There was an initial hydrophilic region followed by a hydrophobic peak in the G protein of HRS virus A2, HRS virus 18537 and the G protein of BRS virus. These two regions together corresponded to the proposed cytoplasmic domain (amino acids 1–37). This was followed by a region of strong hydrophobicity, corresponding to the proposed transmembrane domain (amino acids 38–66). The remainder of the protein was mainly hydrophilic, corresponding to the proposed extracellular domain (amino acids 67–257, 292, or 298). This hydrophilic extracellular domain was interrupted in all three G proteins by a short region of hydrophobicity (amino acids 166–188) which corresponded to the area containing the four conserved cysteine residues.

The BRS virus G mRNA contained two open reading frames in addition to the major open reading frame. One open reading frame began at nucleotide 212, ended at nucleotide 352, and coded for a predicted polypeptide of 46 amino acids. The other and larger of the two was in the same coding frame as the first but began at nucleotide 380 and ended at nucleotide 814. This open reading frame coded for a predicted polypeptide of 144 amino acids.

6.2.3. Construction and Characterization of Recombinant Vaccinia Virus Vectors Containing the BRS Virus G Gene A cDNA containing the complete major open reading frame of the BRS virus G mRNA was inserted into a plasmid, pIB176-192, designed for the construction of vaccinia virus recombinants. The plasmid pIB176-192 is similar to recombination plasmids described previously (Ball, et al., 1986, Proc. Natl. Acad. Sci. USA 83:246–250) which contain a portion of the HindIII J fragment of vaccinia virus with the 7.5K promoter inserted into the thymidine kinase (tk) gene. However, in the case of pIB176-192, the 1710 base pair fragment between the HindIII and PvuII sites of the HindIII J fragment was inserted between the HindIII and SmaI sites of pIB176 and the 7.5K promoter directs transcription in the direction opposite of the tk promoter. The cDNA of the BRS virus G mRNA was inserted downstream of the major transcriptional start site of the 7.5K promoter. The HindIII J fragment containing the inserted BRS virus G gene was inserted into the genome of vaccinia virus (Copenhagen strain) by homologous recombination (Stott, et al., 1986, J. Virol. 60:607–613). Thymidine kinase negative recombinant vaccinia viruses (rVV) were identified by hybridization of recombinant viral DNA with a probe specific for the BRS virus G gene and selected by three rounds of plaque purification. Recombinant vaccinia virus G642 and G4567 contained the BRS virus G gene in the forward and reverse orientation with respect to the 7.5K promoter, respectively. The genome structures of recombinant vaccinia viruses were confirmed by southern blot analysis of digests of vaccinia virus core DNA to confirm that the BRS virus G gene was inserted within the tk gene of the recombinant viruses.

6.2.4. Analysis of Proteins from Cells Infected with Recombinant Vaccinia Virus Containing the BRS Virus G Gene The ability of the recombinant vaccinia virus containing the BRS virus G gene to express the BRS virus G protein was examined in BT cells. The proteins from BT cells infected with either BRS virus, wild type vaccinia virus, or the recombinant vaccinia viruses containing the BRS virus G gene were analyzed by western blot analysis with BRS virus 391-2 specific antiserum because the BRS virus G protein is not readily labeled with [$^{35}$S]-methionine due to the scarcity of this amino acid in the BRS virus G amino acid sequence, and the fact that the 391-2 antiserum does not work for immunoprecipitation. The 391-2 antiserum was shown previously to recognize the BRS virus G protein in a western blot analysis of proteins from BRS virus infected cells (Lerch et al., 1989, J. Virol. 63:833–840). The serum recognized two proteins present in rVV G642 (forward orientation) infected cells (FIG. 6, lane G642+) but not in rVV G4567 (reverse orientation) or wild type vaccinia infected cells (FIG. 6, lanes G4567-and VV respectively). The two proteins produced in rVV G642 infected cells comigrated with proteins recognized by the antiserum in BRS virus infected cells. One of the proteins in rVV G642 infected cells comigrated with the mature BRS virus G protein, migrating as a broad band between the 68 kD and 97 kD protein markers. The other protein migrated at approximately 43 kD.

6.2.5. Surface Expression of BRS Virus G Protein Expressed from Recombinant Vaccinia Viruses The G protein is a glycoprotein expressed on the surface of infected cells and incorporated in the membranes of virions (Huang, 1985, Virus Res. 2:157–173). In order to determine if the BRS virus G protein expressed in the recombinant vaccinia virus infected cells was transported to and expressed on the surface of infected cells, indirect immunofluorescent staining was performed on recombinant virus infected cells. BT cells were found to be extremely sensitive to vaccinia virus infection. There was high background fluorescence and very few cells survived the staining procedure. For these reasons immunofluorescence staining was done on recombinant virus infected HEp-2 cells. HEp-2 cells that were infected with recombinant G642 (FIG. 7, panel rVVG) demonstrated specific surface fluorescence which was not present in either uninfected cells (FIG. 7, panel M) or wild type vaccinia virus infected cells (FIG. 7, panel VV).

6.3. Discussion

The G protein of respiratory syncytial virus is an unusual viral glycoprotein for a variety of reasons. Although it has been characterized as the attachment protein for HRS virus (Levine et al., 1987, J. Gen. Virol. 68:2521–2524), it lacks both neuraminidase and hemagglutinating activities observed in the attachment proteins of other viruses in the Paramyxovirus family (Gruber and Levine, 1983, J. Gen. Virol. 64:825–832; Richman et al., 1971, Appl. Microbiol. 21: 1099). Evidence suggests the HRS virus G protein is extensively glycosylated with approximately 55% of the mass of the mature protein estimated to be due to addition of O-linked oligosaccharide side chains (Lambert, 1988, Virology 164:458–466). The G protein of BRS virus has been shown to be antigenically distinct from the HRS virus G protein (Lerch et al., 1989, J. Virol. 63:833–840; Orvell et al., 1987, J. Gen. Virol. 68:3125–3135). In addition, with the exception of one report (Matumoto et al., Arch. Gesamte Virusforsch 44:280–290), BRS virus is unable to productively infect cells of human origin while HRS virus infects both human and bovine cells. It is possible that the difference in host range between BRS and HRS viruses may be reflected in the amino acid sequence differences observed in the attachment proteins.

In order to further examine the differences between the BRS virus and the HRS virus G proteins the nucleotide sequence of the BRS virus G protein mRNA from cDNA clones was determined. The BRS virus G mRNA was smaller than the G mRNAs of the HRS viruses, and shared 51% sequence identity with the G mRNAs of the HRS viruses sequenced to date. The consensus viral gene start and end sequences observed in HRS virus genes were conserved in the BRS virus G mRNA, as was the position of the initiation codon with respect to the initiation codon of the HRS virus G mRNA. The BRS virus G mRNA had a larger 3' noncoding region, which combined with the smaller size of the BRS virus G mRNA, resulted in a major open reading frame which coded for a polypeptide of 257 amino acids and having an estimated molecular weight of 28 kDa. This compares to polypeptides of 298 and 292 amino acids coded for by the G mRNAs of HRS virus subgroup A and subgroup B viruses, respectively, and estimated molecular weights of about 32 kDa for each. The size of the predicted BRS virus G polypeptide when compared to the estimated size of the mature BRS virus G protein found in infected cells suggested that there is extensive modification of the BRS virus G polypeptide.

Studies using endoglycosidases, inhibitors of carbohydrate addition, and a cell line deficient in O-linked glycosylation have shown that the HRS virus G protein is extensively glycosylated with both N- and O-linked carbohydrate side chains (Lambert, 1988, Virology 164:458–466). The mature BRS virus G protein from infected cells was shown to be glycosylated and had an electrophoretic mobility similar to the 90 kDa HRS virus G protein whereas the predicted amino acid sequence for the polypeptide indicated a protein of 28 kDa (Lerch et al., 1989, J. Virol. 63:833–840; Westenbrink et al., 1989, J. Gen. Virol. 70:591–601). This suggested the BRS virus G protein was also extensively glycosylated as is the HRS virus G protein. The predicted amino acid sequence of the BRS virus G protein had high levels of serine and threonine (25%), similar to the levels for the HRS virus G proteins (30% and 28% for subgroup A and B, respectively) although the actual number of potential O-glycosylation sites for BRS virus (66) is lower than the 91 potential sites found in HRS virus subgroup A (Johnson et al., 1987, Proc. Natl. Acad. Sci. U.S.A. 84:5625–5629; Satake, et al., 1985, Nucleic Acids Res. 13:7795–7812; Wertz et al., 1985, Proc. Natl. Acad. Sci. U.S.A. 82:4075–4079). The high content of serine and threonine in the deduced BRS virus G amino acid sequence suggests that the BRS virus G protein also has the potential for extensive O-linked glycosylation.

Although the overall amino acid composition of the BRS virus G protein was similar to that of the HRS virus G protein, the BRS virus G amino acid sequence had a lower level of overall amino acid identity with the HRS virus G proteins of either the subgroup A or B viruses (Johnson et al., 1987, Proc. Natl. Acad. Sci. U.S.A. 84:5625–5629). There was only 29–30% identity between the BRS virus G protein and the G protein of either subgroup A or B HRS viruses, whereas there is 53% amino acid identity when the G proteins of the HRS virus subgroup A and subgroup B viruses are compared (Johnson et al., 1987, Proc. Natl. Acad. Sci. U.S.A. 84:5625–5629). Higher levels of amino acid identity were present between the BRS virus G protein and the HRS virus G proteins in the proposed cytoplasmic and transmembrane domains, but again this level was not as high as that found when comparing those regions of the G proteins of subgroup A and B HRS viruses (FIG. 4). The fact that the BRS virus G protein amino acid sequence is not significantly more closely related to the G protein amino acid sequence of either HRS virus subgroup A or B suggests that the human and bovine respiratory syncytial viruses diverged prior to the emergence of the HRS virus A and B subgroups and that they should be classified in separate Pneumovirus subgroups.

The predicted amino acid sequence of the BRS virus G protein showed that the BRS virus and HRS virus G proteins shared only 29–30% amino acid identity. In spite of these differences, the hydropathy profiles of the two proteins showed strong similarities suggesting the possibility of similar overall structural features.

Johnson et al. (1987, Proc. Natl. Acad. Sci. U.S.A. 84:5625–5629) suggested that a conserved 13 amino acid region found in the extracellular domain of the G protein of HRS viruses could be a candidate for a receptor binding site. The fact that this conserved region is not conserved in the G protein of BRS virus could relate to the host specificity of BRS virus. The four conserved cysteine residues found in the G protein of both the BRS virus and HRS viruses could result in a similar secondary structure among the G proteins with specific differences in the conserved region changing the host specificity. Convalescent calf serum has suggested the possibility that BRS virus may have antigenic subgroups as does HRS virus (Lerch et al., 1989, J. Virol. 63:833–840).

Recombinant vaccinia viruses containing a cDNA insert to the BRS virus G gene expressed the BRS virus G protein. This BRS virus G protein had an electrophoretic mobility in SDS-polyacrylamide gels which was similar to the G protein from BRS virus infected cells. Antiserum specific for BRS virus 391-2 recognized the BRS virus G protein produced by recombinant vaccinia virus in infected cells as shown by western blot analysis. The BRS virus G protein expressed from the recombinant vaccinia virus was transported to and expressed on the surface of infected cells as shown by surface immunofluorescence.

7. EXAMPLE

Nucleotide Sequence Analysis of Bovine Respiratory Syncytial Virus Fusion Protein mRNA and a Recombinant Vaccinia Virus

7.1. Materials and Methods

7.1.1. Virus and Cells

The growth and propagation of BRS virus 391-2, wild type (Copenhagen strain) and recombinant vaccinia viruses, bovine nasal turbinate (BT) cells, HEp-2 cells, and thymidine kinase negative (tk⁻) 143B cells were as described in Hruby and Ball (1981, J. Virol. 40:456–464; Stott et al., 1986, J. Virol. 60: 607–613; Lerch et al., 1989, J. Virol. 63:833–840).

7.1.2. Protein Labeling and Harvest of BRS Virus Infected Cells

Cell monolayers of bovine nasal turbinate (BT) cells were mock, BRS virus or HRS virus-infected. Tunicamycin (1.5

µg/ml, Boehringer Mannheim) was added to the medium covering the cells at 25 hours post infection where indicated. After one hour the medium was removed from all monolayers and replaced with DMEM lacking methionine (Gibco). Tunicamycin was re-added where indicated. Following a 30 minute incubation, [$^{35}$]methionine 100 µCi/ml, New England Nuclear) was added to the medium. The cells were incubated for two hours and proteins harvested as described in Lerch et al., 1989, J. Virol. 63:833–840. Virus-specific proteins were immunoprecipitated as described in Wertz et al., (1985, Proc. Natl. Acad. Sci. U.S.A. 82:4075–4079) using Wellcome anti-RS serum (Wellcome Reagents Ltd.). Proteins were analyzed by SDS-polyactylamide gel electrophoresis (SDS-PAGE) (Laemmli, 1970, Nature (London) 227:680–685), and detected by fluorography (Davis and Wertz, 1982, J. Virol. 41:821–832).

7.1.3. cDNA Synthesis, Molecular Cloning, and Identification of F Specific cDNA Clones cDNAs were synthesized using the strand replacement method of Gubler and Hoffman (1983, Gene 25:263–269) as described in D'Alessio et al. (1987, Focus 9:1–4). T4 DNA polymerase (BRL) was used to make the ends of the cDNAs blunt (Maniatis et al., 1982, in "Molecular Cloning: a laboratory manual," Cold Spring Harbor Laboratory, Cold Spring Harbor, N.Y.). The cDNAs were ligated into M13mp19 replicative form (RF) DNA, which had been digested with SmaI and treated with calf intestinal alkaline phosphatase (Maniatis et al., supra), and transfected into competent E. coli DH5 αF' cells (Bethesda Research Laboratories) (Hanahan, 1983, J. Mol. Biol. 166:557–580). M13mp19 phage containing BRS virus F specific inserts were identified by dot blot hybridization of phage DNA (Davis et al., 1986, "Basic Methods in Molecular Biology. Elsevier Science Publishing Co., Inc., New York, N.Y.) probed with a previously identified BRS virus F gene specific clone (Lerch et al., 1989, J. Virol. 63:833–840) which had been labeled by nick translation (Rigby et al., 1977, J. Mol. Biol. 113:237–251). Growth and manipulations of M13mp19 and recombinant phage were as described by Messing (1983, Meth. Enzymol. 101:20–78).

7.1.4. Nucleotide Sequencing and Primer Extension on RNA

Dideoxynucleotide sequencing using the Klenow fragment of E. coli DNA polymerase I (Pharmacia) or a modified T7 DNA Polymerase (Sequenase, U.S. Biochemicals) was done as described in Tabor and Richardson (1987, Proc. Natl. Acad. Sci. U.S.A. 84:4746–4771) and Lim and Pene (1988, Gene Anal. Tech. 5:32–39) using an M13 sequencing primer (New England Biolabs). Extension of a synthetic DNA primer, complementary to bases 267 to 284 of the BRS virus F mRNA, was done on BRS virus mRNA using Avian myeloblastosis virus (AMV) reverse transcriptase (Molecular Genetic Resources) (Air, 1979, Virology 97:468–472). BRS virus mRNA used a cemplate in the primer extension on RNA and was harvested as described for mRNA used for cDNA synthesis (Lerch et al., 1989, J. Virol. 63:833–840). Nucleotide sequencing and primer extension were done using [α-$^{35}$S] dATP (Amersham) and polyacrylamide-urea gradient gel electrophoresis as described by Biggin et al. (1983, Proc. Natl. Acad. Sci. U.S.A. 80:3963–3965). The nucleotide sequence was analyzed using the University of Wisconsin Genetics Computer Group software package (Devereux et al., 1984, Nucl. Acids Res. 12:387–395).

7.1.5. Synthesis and Cloning of a Complete cDNA to the BRS Virus F mRNA

A cDNA containing the complete major open reading frame of the BRS virus F mRNA was synthesized using a specific synthetic oligonucleotide for second strand synthesis. The nucleotide sequence for this oligonucleotide was determined from sequence analysis of BRS virus mRNAs. First strand synthesis occurred as described in D'Alessio et al. (1987, Focus 9:1–4). Following synthesis, the RNA template was digested with RNase A (1 .mu.g/.mu.1) for thirty minutes at 37.degree. C. The resulting single-stranded cDNAs were isolated by phenol extraction and ethanol precipitation. The oligonucleotide used for second strand synthesis had the sequence .sup.5'CACGGATCCACAAGTATGTCCAACC.sup.3' (SEQ ID No. 7) with the 5' first nine bases of the oligonucleotide containing a BamHI restriction enzyme site. The single-stranded cDNAs were mixed with the oligonucleotide (50 .mu.g/ml), heated to 100.degree. C. for one minute and placed on ice. AMV reverse transcriptase was used to synthesize the second strand of the cDNAs in a reaction [50 mM Tris-HCl (pH8.0), 50 mM KCl, 5mMgCl2, 10 mM dithiothreitol, 1.6 mM dNTPs, 100U AMV reverse transcriptase] that was incubated for one hour at 50.degree. C. The cDNAs were separated from protein by phenol extraction, recovered by ethanol precipitation, and the ends made blunt with T4 DNA polymerase. Blunt-ended cDNAs were then digested with the restriction enzyme BamHI (Bethesda Research Laboratories) and separated from protein by phenol extraction. M13mp18 RF DNA, that was digested with BamHI and SmaI and treated with calf intestinal phosphatase, was added to the cDNAs and recovered by ethanol precipitation. The cDNAs and vector were ligated and transfected into competent DH5.alpha.F' cells (Bethesda Research Laboratories) as described in Hanahan (1983, J. Mol. Biol. 166:557–580).

7.1.6. Construction and Isolation of Recombinant Vaccinia Virus Vectors

A complete cDNA clone, F20, corresponding to the BRS virus F mRNA was subcloned into a recombination plasmid, pIBI76-192, by digestion with BamHI and KpnI, treatment with T4 DNA polymerase to make the ends of the cDNA blunt, and ligation into the unique SmaI site of pIBI76-192. The plasmid pIBI76-192 is similar to recombination plasmids described in Ball et al. (1986, Proc. Natl. Acad. Sci. U.S.A. 83:246–250). In the case of pIBI76-192, base pairs (bp) 1 to 1710 of the HindIII J fragment of vaccinia virus was inserted between the HindIII and SmaI sites of pIBI76 (International Biotechnology Inc.). A 280 bp. fragment of DNA that contains the 7.5k promoter of vaccinia virus was inserted into the EcoRI site (bp 670 of the HindIII J fragment) of the vaccinia virus thymidine kinase (tk) gene (bp 502 to 1070 of the HindIII J fragment, Weir and Moss, 1983, J. Virol. 46:530–537). The orientation of this promoter was such that it directed transcription from right to left on the conventional vaccinia virus map, opposite to the direction of transcription of the vaccinia virus tk gene. The unique SmaI site in pIBI76-192 was downstream of the major transcriptional start site of the 7.5K promoter.

The isolation of recombinant vaccinia viruses containing the BRS virus F mRNA sequence was as described in Stott et al. (1986, J. Virol. 60:607–613) except that the recombinant viruses were identified using the blot procedure of Lavi and Ektin (1981, Carcinogenesis 2:417–423).

7.1.7. Characterization of Recombinant Vaccinia Virus Vectors

DNA from vaccinia virus cores isolated from wild type and recombinant viruses was prepared for southern blot analysis as described by Esposito et al. (1981, J. Virol. Meth. 2:175–179). Restriction enzyme digestion, southern blot analysis, and radioactive labeling of DNA by nick translation were as described in Section 6, supra. Metabolic labeling of proteins from wild type and recombinant vaccinia virus infected cells was as above except that infected cells were exposed to label for three hours starting at three hours postinfection. Proteins were analyzed by SDS-polyacrylamide gel electrophoresis using standard procedures. Immunoprecipitation of virus-specific proteins was as described in Wertz et al. (1985, Proc. Natl. Acad. Sci. U.S.A. 82:4075–4079) using Wellcome anti-RS serum (Wellcome Reagents Ltd.). For immunofluorescence HEp-2 cells were grown on glass cover slips. Cells were infected with wild type or recombinant vaccinia viruses (moi=10) and at 24 hours postinfection the cells were stained by indirect immunofluorescence using anti-BRS virus 391-2 serum (Lerch et al., 1989, J. Virol. 63:833–840) as a first antibody followed by fluorescein conjugated anti-bovine IgG (H+L). Fluorescence was observed through a fluorescence microscope available from Nikon.

7.2. Results

7.2.1. Nucleic Acid Sequence and Comparison

In order to determine the complete nucleotide sequence of the BRS virus F mRNA, cDNA clones in M13 phage vectors were isolated and their nucleotide sequence analyzed. The BRS virus F mRNA sequence was determined from eight clones derived independently from four separate cDNA synthesis reactions. The areas of the BRS virus F mRNA sequence determined from the different clones are shown in FIG. 8. The majority of the sequence was determined from three clones, FB3, FB5 and F20. Clone F20 is a full length BRS virus F cDNA which was synthesized using oligonucleotide specific for the 5' end of the BRS virus F mRNA. The inserts from clones FB3, FB5 and F20 were excised using the restriction enzymes PstI and KpnI, which do not cut within the inserts, and subcloned into M13mp18 RF DNA to sequence from the opposite end of the cDNA. In addition, restriction fragments of the inserts were subcloned into M13mp18 and mp19 RF DNA to allow for determination of the sequence of the middle of the cDNAs. Clone F20 was digested with the restriction enzymes AlwNI, PflMI, EcoRV, or HpaI, and clones FB3 and FB5 were digested with the restriction enzyme EcoRI. The 5' end of the BRS virus F mRNA sequence was determined by extension of a DNA oligonucleotide on mRNA from BRS virus infected cells. The sequence for the oligonucleotide, complementary to bases 267 to 284 of the BRS virus F mRNA, was determined from the sequence provided by the cDNA clones. Clones F29, FB2, F138 and FB1, all 750 nucleotides or less were not sequenced extensively.

The BRS virus F mRNA contained 1899 nucleotides excluding a polyadenylate tail (FIGS. 9A–C) (SEQ ID No. 3). Seven bases at the exact 5' end of the mRNA could not be determined due to strong stop signals in all four nucleotide reactions for each base during primer extension on mRNA. The sequence at the 3' end of the BRS virus F mRNA conformed to one of the two consensus gene-end sequences, 5' . . . AGU-.sub.U.sup.A AU-.sub. U.sup.A UpolyA3', found at the end of all IRS virus genes (Collins et al., 1986, Proc. Natl. Acad. Sci. U.S.A. 83:4594–4598) and at the 3' end of the BRS virus G mRNA. The BRS virus F mRNA had a single major open reading frame starting with an initiation codon beginning at nucleotide 14 and extending to a termination codon at nucleotide 1736. There was a 161 nucleotide noncoding region at the 3' end prior to the 3' polyadenylate tract (FIGS. 9A–C) (SEQ ID No. 3).

The nucleotide sequence of the BRS virus F mRNA was compared to the published sequences for the F mRNA of HRS virus A2 (Collins et al., 1986, Proc. Natl. Acad. Sci. U.S.A. 83:4594–4598), Long (Lopez et al., 1988, Virus Res. 10:249–262), RSS-2 (Baybutt and Pringle, 1987, J. Gen. Vir. 68:2789–2796) and 18537 (Johnson and Collins, 1988, J. Gen. Virol. 69:2623–2628) to determine the extent of nucleic acid identity among the different F mRNA sequences (Table 1).

TABLE 1

NUCLEIC ACID IDENTITY BETWEEN THE FUSION
PROTEIN GENES OF RESPIRATORY SYNCYTIAL VIRUSES

| VIRUSES COMPARED | (% IDENTITY WITHIN INDICATED AREAS) | | |
| --- | --- | --- | --- |
| | TOTAL | CODING SEQUENCE | 3' NONCODING SEQUENCE |
| HRS VIRUS, SUBGROUP A VS HRS VIRUS, SUBGROUP A | 97–98 | 97 | 98–99 |
| HRS VIRUS, SUBGROUP B VS HRS VIRUS, SUBGROUP A | 79 | 82 | 47 |
| BRS VIRUS VS HRS VIRUS, SUBGROUP A | 72 | 75 | 36–37 |
| BRS VIRUS VS HRS VIRUS, SUBGROUP B | 71 | 74 | 39 |

HRS virus A2, Long and RSS-2 are subgroup A viruses, and 18537 is a subgroup B virus (Anderson et al., 1985, J. Infect. Dis. 151:626–633; Mufson et al., 1985, J. Gen. Virol. 66:2111–2124). The level of nucleic acid identity between the F mRNAs of BRS virus and HRS viruses (71.5%) was similar to that observed when comparing the F mRNAs of the two HRS virus subgroups (79%). Both the level of identity between the F mRNAs of BRS virus and HRS virus, and between the F mRNAs of the two HRS virus subgroups was lower than the level of identity between the F mRNAs of HRS viruses within the same subgroups (97–98%). The level of nucleotide sequence identity between the BRS virus and HRS viruses in the 3' noncoding region of the F sequence was 37.5% compared to 74.5% in the F sequence coding region. This was similar to the levels of identity in 3' noncoding and coding regions, 47% and 82% respectively, when comparing the F sequences of the subgroup A HRS viruses to the subgroup B HRS virus. There was variation in the nucleotides at two positions in the F mRNA sequence. In one clone, clone F20, nucleotides 455 and 473 were a G and C, respectively, rather than the A and G observed in the other clone and shown in the sequence (FIGS. 9A–C).

7.2.2. Predicted Amino Acid Sequence of the BRS Virus F Protein and Comparison to the F Proteins Sequences of HRS Virus The open reading frame of the BRS virus F mRNA predicted a polypeptide of 574 amino acids. The amino acid sequence of this polypeptide is shown below the mRNA sequence in FIGS. 9A–C (SEQ ID No. 4). The estimated molecular weight of the predicted BRS virus F polypeptide was 63.8 kDA. A hydropathy profile of the predicted polypeptide indicated strong hydrophobic regions at the amino terminus, corresponding to residues 1 through 26, and close to the carboxy terminus, corresponding to residues 522 through 549 (FIG. 10). The hydropathy profile and amino acid sequence suggested domains in the BRS virus F protein similar to those described for the HS virus F protein, including an amino terminal signal peptide region (residues 1–26), carboxy terminal anchor region (residues 522–549), and putative cleavage sequence (residues 131–136) that generates the F.sub.1 and F.sub.2 polypeptides (see FIGS. 10 and 11A–C). There were three potential sites for addition of N-linked carbohydrate side chains, two in the proposed F.sub.2 polypeptide, and one in the proposed F.sub.1 polypeptide (FIGS. 9A–C) (SEQ ID No. 4).

The predicted BRS virus F amino acid sequence was compared to the predicted amino acid sequences of the F polypeptides of HRS viruses A2 (Collins et al., 1984, Proc. Natl. Acad. Sci., U.S.A. 81:7i683–7i687), Long (Lopez et al., 1988, Virus Res. 10:249–262), RSS-2 (Baybutt and Pringle, 1987, J. Gen. Virol. 68:2789–2796) and 18537 (Johnson and Collins, 1988, J. Gen. Virol. 69:2623–2628) (FIGS. 11A–C). The BRS virus F polypeptide was 574 amino acids as are all four HRS virus F polypeptides. Proposed carboxy terminal hydrophobic anchor (residues 522–549) and amino terminal signal regions (residues 1–26) present in the BRS virus F protein were similar to those in the HRS virus F proteins. In addition, the sequence of Lys-Lys-Arg-Lys-Arg-Arg at residues 131 to 136 in the BRS virus F protein represented a proposed cleavage signal. This sequence was identical to the proposed cleavage signals in all the HRS virus F proteins. The cleavage sequence in the BRS virus F protein was followed by a stretch of hydrophobic residues (residues 137–158) that would represent the amino terminus of the $F_1$ polypeptide following cleavage. The nucleotide differences in clone F20 would result in amino acids residues 148 and 154, part of the proposed $F_1$ amino terminus, changing from Val to Ile, and Leu to Val, respectively. These differences would result in the amino acids at these two positions in the BRS virus F protein being identical to the corresponding amino acid positions in the HRS virus F proteins.

With the exception of one cysteine residue (residue 25) in the proposed amino terminal signal peptide, all the cysteine residues were conserved in position among the BRS virus and HRS virus F proteins. This includes the cysteine residue at position 550, which has been shown to be the site of covalent attachment of palmitate to the human RS virus F protein (Arumugham et al., 1989, J. Biol. Chem. 264: 10339–10342). There was a single potential site for N-linked glycosylation (residue 500) in the $F_1$ polypeptide of the BRS virus F protein that was conserved in all the HRS virus F proteins (FIGS. 11A–C). There were two potential sites for N-linked glycosylation (residues 27 and 120) in the BRS virus $F_2$ polypeptide (FIGS. 9A–C and 11A–C). The potential site at residue 27 was conserved among the BRS virus and HRS virus F proteins (FIGS. 11A–C). However, the HRS virus $F_2$ polypeptides contained a total of four or five potential sites, depending on the isolate, and the position of the remaining potential site for N-linked glycosylation in the BRS virus $F_2$ polypeptide was not conserved in all the HRS virus $F_2$ polypeptides (FIGS. 11A–C). The existence of only two potential N-linked glycosylation sites on the BRS virus $F_2$ polypeptide was consistent with the earlier observation that there were differences in electrophoretic mobility of the BRS virus and HRS virus $F_2$ polypeptides (Lerch et al., 1989, J. Virol. 63:833–840).

The amino acid identity between the F proteins of the different viruses is shown for the different regions of the F protein (Table 2).

TABLE 2

AMINO ACID IDENTITY BETWEEN THE FUSION PROTEINS OF RESPIRATORY SYNCYTIAL VIRUSES

| | (% IDENTITY WITHIN INDICATED AREAS) | | | |
|---|---|---|---|---|
| VIRUSES COMPARED | TOTAL | $F_1$ PEPTIDE | $F_2$ PEPTIDE | SIGNAL PEPTIDE |
| HRS VIRUS, SUBGROUP A VS HRS VIRUS, SUBGROUP A | 97–98 | 98–99 | 93–96 | 81–88 |
| HRS VIRUS, SUBGROUP A HRS VIRUS, SUBGROUP B | 89 | 93 | 83 | 36 |
| VS HRS VIRUS, SUBGROUP A BRS VIRUS | 80 | 88 | 67–69 | 4 |
| VS HRS VIRUS, SUBGROUP A BRS VIRUS | 81 | 88 | 68 | 12 |
| VS HRS VIRUS, SUBGROUP B | | | | |

HRS viruses A2, Long, and RSS-2 are subgroup A viruses, and 18537 is a subgroup B virus (Anderson et al., 1985, J. Infect. Dis. 151:626–633); Mufson et al., 1985, J. Gen. Virol. 66:2111–2124). Although the greatest extent of variation was in the proposed signal peptide region (residues 1–26), the overall hydrophobicity of this region was conserved in the BRS virus F protein (FIG. 10). The proposed $F_2$ polypeptide of the BRS virus F protein showed a lower level of identity to the F2 polypeptides than is present between the $F_2$ polypeptides of the HRS virus A and B subgroups (Johnson and Collins, 1988, J. Gen. Virol. 2623–2628). In contrast, the levels of identity between the different $F_1$ polypeptides were similar whether comparing BRS virus to HRS virus or comparing two HRS virus subgroups.

7.2.3. Effects of Tunicamycin on Electrephoretic Mobility of BRS Virus F Protein To determine whether previously observed glycosylation of the BRS virus F protein (Lerch et al., 1989, J. Virol. 63:833–840) was due to N-linked glycosylation, the electrophoretic mobility of the BRS virus F protein radioactively labeled in the presence and absence of tunicamycin, an inhibitor of N-linked glycosylation, was examined. Proteins in BRS virus, HRS virus, and mock infected cells were radioactively labeled by exposure to [$^{35}$S]methionine in the presence and absence of tunicamycin, immunoprecipitated and separated by SDS-polyacrylamide gel electrophoresis. BRS virus F protein labeled in the presence of tunicamycin demonstrated a change in electrophoretic mobility compared to BRS virus F protein labeled in the absence of tunicamycin (FIG. 12, lanes $B_T$ and B). In addition, the BRS virus $F_0$, $F_1$ and $F_2$ polypeptides synthesized in the presence of tunicamycin had electrophoretic mobilities similar to the respective HRS virus $F_0$, $F_1$ and $F_2$ polypeptides synthesized in the presence of tunicamycin (FIG. 12, lanes $H_T$ and $B_T$). These results indicated that the BRS virus F protein was glycosylated via N-linked carbohydrate additions, and the observed differences in the electrophoretic mobility of the BRS virus and HRS virus $F_2$ polypeptides are due to differences in the extent of glycosylation as predicted by the deduced amino acid sequence (FIGS. 11A–C).

7.2.4. Construction and Isolation of Recombinant Vaccinia Virus Vectors Containing the BRS Virus Gene To facilitate the study of the role of individual proteins of BRS virus in eliciting a protective immune response in the host, the BRS virus F gene was placed in a vaccinia virus expression vector. A cDNA (F20) containing the complete major open reading frame of the BRS virus F mRNA was inserted into a plasmid, pIBI76-192, designed for construction of vaccinia virus recombinants. The plasmid pIBI76-192 is similar to recombination plasmids described in Ball et al. (1986, Proc. Natl. Acad. Sci. U.S.A. 83:246–250) that contain a portion of the HindIII J fragment of vaccinia virus with the 7.5K promoter inserted into the thymidine kinase (tk) gene. However, in the case of pIBI76-192, the 7.5K promoter directs transcription in the opposite direction of transcription of the tk gene. The cDNA of the BRS virus F mRNA was inserted downstream of the major transcriptional start site of the 7.5K promoter. The HindIII J fragment containing the inserted BRS virus F gene was inserted into the genome of vaccinia virus (Copenhagen strain) by homologous recombination (Stott et al., 1986, J. Virol. 60:607–613). Thymidine kinase negative recombinant vaccinia viruses (rVV) were identified by hybridization of recombinant viruses with a probe specific for the BRS virus F gene and selected by three rounds of plaque purification. Recombinant vaccinia virus F464 and F1597 contained the BRS virus F gene in the forward and reverse orientation with respect to the 7.5K promoter, respectively. The genome structures of recombinant vaccinia viruses were examined by Southern blot analysis of restriction enzyme digests of vaccinia virus core DNA. These experiments confirmed that the ERS virus F gene was inserted within the tk gene of the recombinant viruses.

7.2.5. Analysis of Proteins from Cells Infected with Recombinant Vaccinia Virus Containing the BRS Virus F Gene The ability of the recombinant vaccinia viruses containing the BRS virus F gene to express the BRS virus F protein was examined in tissue culture cells. BT cells were infected with either BRS virus, wild type vaccinia virus, or the recombinant vaccinia viruses containing the BRS virus F gene in the positive or negative orientation with respect to the promoter. The proteins in cells were labeled by incorporation of [$^{35}$]methionine, harvested, and then immunoprecipitated with the Wellcome anti-RS serum and separated by SDS-polyacrylamide gel electrophoresis. The recombinant vaccinia virus F464 (forward orientation) produced at least two proteins in infected cells which were precipitated by the Wellcome anti-RS serum (FIG. 13, lane F464+), and were not present in wild type vaccinia virus infected cells (FIG. 13, lane VV) or rVV F1597 (reverse orientation) infected cells (FIG. 13, lane F1597–). The two proteins specific to rVVF464 infected cells had electrophoretic mobilities identical to the BRS virus $F_0$ and $F_1$ polypeptides. A cellular protein that was precipitated by the serum (FIG. 12, lane M), had an electrophoretic mobility similar to the BRS virus $F_2$ polypeptide and inhibited the detection of an $F_2$ polypeptide in rVV F464 infected cells. It was presumed that if the $F_0$ protein was produced and cleaved to generate the $F_1$ polypeptide, the $F_2$ polypeptide was also present even though it could not be visualized.

An additional protein that had been previously observed in BRS virus infected cells (Lerch et al., 1989, J. Virol. 63:833–840) and was slightly larger than the BRS virus 22K protein was observed in rVV F464 infected cells (FIG. 13, lane F464+). This additional protein was only produced in BRS virus infected cells or rVV F464 infected cells and was immunoprecipitated by the Wellcome antiserum. This result indicated that the additional protein might have been either a specific cleavage fragment of the BRS virus F protein or interacted with the BRS virus F protein.

7.2.6. Glycosylation of the BRS Virus F Protein Expressed from a Recombinant Vaccinia Virus In order to determine whether the F polypeptides synthesized in the recombinant virus infected cells were glycosylated in a manner similar to the authentic BRS virus F polypeptides, the proteins in rVV F464 infected BT cells were labeled with [$^{35}$S]methionine in the presence and absence of tunicamycin. These proteins were compared to similarly labeled proteins from BRS virus infected BT cells by immunoprecipitation and SDS-polyacrylamide gel electrophoresis (FIG. 14). In the presence of tunicamycin, the $F_0$ and $F_1$ polypeptides produced in rVV F464 virus infected cells had faster electrophoretic mobilities than their counterparts synthesized in the absence of tunicamycin (FIG. 14, compare lane $F_T$ to lane F), and had electrophoretic mobilities identical to the unglycosylated $F_0$ and $F_1$ polypeptides from BRS virus infected cells (FIG. 13, lane $F_T$ compared to lane $B_T$). In the presence of tunicamycin, the protein band from recombinant virus infected cells which presumably contained the BRS virus $F_2$ polypeptide along with a cellular protein disappeared, and there was an increase in intensity of a band at the bottom of the gel (FIG. 14, lane $F_T$) where the unglycosylated BRS virus $F_2$ migrates (see FIG. 12).

7.2.7. Cell Surface Expression of the BRS Virus F Protein Expressed from Recombinant Vaccinia Virus The HRS virus F glycoprotein is expressed on the surface of infected cells and incorporated in the membranes of virions (Huang, 1983, "The genome and gene products of human respiratory syncytial virus" Univ. of North Carolina at Chapel Hill; Huang et al., 1985, 2:157–173). In order to determine if the BRS virus F protein expressed in the recombinant vaccinia virus infected cells was transported to and expressed on the surface of infected cells, recombinant vaccinia virus infected cells were examined by indirect immunofluorescence staining. BT cells were extremely sensitive to vaccinia virus infection and could not be used for immunofluorescence without high background fluorescence. For this reason immunofluorescence was carried out on recombinant virus infected HEp-2 cells. The antiserum used in the immunofluorescence was BRS virus 391-2 specific antiserum which was shown previously to recognize the BRS virus F protein in Western blot analysis of proteins from BRS virus infected cells (Lerch et al., 1989, J. Virol. 63:833–840). This antisera was specific in immunofluorescence assays for BRS virus infected, but not uninfected cells. HEp-2 cells that were infected with recombinant F-464 (FIG. 15, panel rVVF) demonstrated specific surface fluorescence that was not present in either uninfected cells (FIG. 15, panel M) or wild type vaccinia virus infected cells (FIG. 15, panel VV).

7.3. Discussion

We have determined the nucleotide sequence of cDNA clones corresponding to the BRS virus F mRNA. The nucleotide sequence and deduced amino acid sequence were compared to that of the corresponding HRS virus sequences. The F mRNA was identical in length, 1899 nucleotides, to the HRS virus A2, Long and RSS-2 F mRNAs (Collins et al., 1984, Proc. Natl Acad. Sci. U.S.A. 81:7683–7687; Baybutt and Pringle, 1987, J. Gen. Virol. 68:2789–2796; Lopez et al. 1988, Virus Res. 10: 249–262). The HRS virus 18537 F mRNA is three nucleotides shorter in the 3' noncoding region (Johnson and Collins, 1988, J. Gen. Virol. 69:2623–2628). The level of nucleic acid identity between the BRS virus and HRS virus F mRNAs was similar to the level between the F mRNAs of the HRS virus subgroup A and B viruses (Johnson and Collins, 1988, J. Gen. Virol. 69:2623–2628). The major open reading frame of the BRS virus F mRNA encoded a predicted protein of 574 amino acids, identical in size to the HRS virus F proteins (Collins et al., 1984, Proc. Natl Acad. Sci. U.S.A. 81:7683–7687; Baybutt and Pringle, 1987, J. Gen. Virol. 68:2789–2796; Johnson and Collins, 1988, J. Gen. Virol. 69:2623–2628; Lopez et al., 1988, Virus Res. 10:249–262). The predicted major structural features of the BRS virus F protein, such as an N-terminal signal, a C-terminal anchor sequence, and a cleavage sequence to yield $F_1$ and $F_2$ polypeptides were conserved with these features in the HRS virus F protein. The deduced amino acid sequence of the BRS virus F protein had 80% overall amino acid identity to the HRS virus F proteins. The BRS virus and HRS virus $F_1$ polypeptides were more conserved, with 88% amino acid identity, than the $F_2$ polypeptides which had 68% amino acid identity. If BRS virus and HRS virus have diverged from a single common ancestor, the lower levels of amino acid identity in $F_2$ compared to $F_1$ suggest there may be different, or fewer constraints on the $F_2$ polypeptide to maintain a specific amino acid sequence than on the $F_1$ polypeptide. Also, the difference in the levels of identity among the human and bovine $F_2$ polypeptides in comparison to the $F_1$ polypeptides suggests that conservation of the exact amino acid sequence of the $F_2$ polypeptide is not as important as that of the $F_1$ polypeptide amino acid sequence in maintaining the structure and function of the F protein. The amino acid sequence of the proposed anchor region and amino terminus of the $F_1$ polypeptide of BRS virus were highly conserved when compared to those sequences in the HRS virus F proteins. The proposed amino terminal signal peptides of the BRS virus and HRS virus F proteins were not conserved in amino acid sequence but were conserved in predicted hydrophobicity.

Synthesis of the BRS virus F polypeptides in the presence of tunicamycin, an inhibitor of N-linked glycosylation, demonstrated that the BRS virus F polypeptides were glycosylated by the addition of N-linked carbohydrate moieties. Also, the $F_2$ polypeptides of BRS virus and HRS virus synthesized in the presence of tunicamycin had the same electrophoretic mobility in SDS-polyacrylamide gels. This indicated the BRS virus and HRS virus $F_2$ polypeptides had differences in the extent of glycosylation. Nucleotide sequence analysis of cDNA clones to the BRS virus F mRNA confirmed a difference in the number of potential glycosylation sites. The deduced BRS virus $F_2$ amino acid sequence contained only two sites for potential N-linked oligosaccharide addition, whereas there are four potential sites in the $F_2$ polypeptide of HRS virus A2.

The use of tunicamycin to inhibit N-linked glycosylation showed that the difference in the electrophoretic mobility of HRS virus and BRS virus $F_1$ polypeptides was not due to glycosylation differences as there were slight differences in the electrophoretic mobilities of the unglycosylated $F_1$ polypeptides of BRS virus and HRS virus. Nucleotide sequence analysis showed the predicted BRS virus $F_1$ amino acid sequence and HRS virus $F_1$ polypeptides were of the same size and both contained one potential site for N-linked oligosaccharide addition. At present it is concluded that slight differences which exist in the amino acid compositions of the BRS virus and HRS virus $F_1$ polypeptides caused the difference in electrophoretic migration. In support of this conclusion is recent work that demonstrates that changing a single amino acid in the vesicular stomatitis virus G protein, while not changing the glycosylation of the protein alters its electrophoretic mobility (Pitta et al., 1989, J. Virol. 63:3801–3809).

The BRS virus F protein, and the HRS virus F proteins have conserved epitopes. Both convalescent calf serum and monoclonal antibodies will recognize the F protein from either virus (Orvell et al., 1987, J. Gen. Virol. 68:3125–3135; Stott et al., 1984, Dev. Biol. Stand. 57:237–244; Kennedy et al., 1988, J. Gen. Virol. 69:3023–3032; Lerch et al., 1989, J. Virol. 63:833–840). Orvell et al. (1987, J. Gen. Virol. 68:3125–3135) found that only 3 out of 35 monoclonal antibodies generated to an HRS virus F protein did not recognize the F protein of three BRS virus strains. In addition, all of the 11 monoclonal antibodies against the F protein which were neutralizing for HRS virus also neutralized the infectivity of the BRS virus strains (Orvell et al., 1987, J. Gen. Virol. 68:3125–3135). Studies using synthetic peptides and monoclonal antibodies have suggested that at least two epitopes on the HRS virus F protein are involved in neutralization of the virus. The epitopes are positioned at amino acids 212 to 232 (Trudel et al., 1987a, J. Gen. Virol. 68:2273–2280; Trudel et al., 1987b, Canad. J. Microbiol. 33:933–938) and amino acids 283 to 299. The first of these epitopes is exactly conserved in the BRS virus F protein. In the second epitope, there are three changes in the BRS virus F protein, all of which are conservative changes. Although both of these epitopes are on the $F_1$ polypeptide, amino acids affecting neutralization have been localized to the $F_2$ polypeptide in the fusion protein of Newcastle disease virus (Totoda et al., 1988, J. Virol. 62:4427–4430; Neyt et al., 1989, J. Virol. 63:952–954).

In contrast to the similarities of the HRS virus and BRS virus F proteins, the G proteins of these viruses are antigenically distinct. All monoclonal antibodies generated against the G protein of either HRS virus subgroup did not recognize the BRS virus G protein (Orvell et al., 1987, J. Gen. Virol. 68:3125–3135). It has been shown that polyclonal convalescent serum from a calf infected with BRS virus, while recognizing the BRS virus G protein, did not recognize the G protein of a HRS virus (Lerch et al., 1989, J. Virol. 63:833–840). The antigenic similarity between the BRS virus and HRS virus F proteins and the difference in antigenic cross reactivity between the BRS virus and HRS virus G proteins was also reflected in the levels of amino acid identity between the homologous proteins of HRS virus and BRS virus. The HRS virus and BRS virus G proteins shared only 30% amino acid identity whereas the F proteins of the two viruses shared 80% amino acid identity. The differences in the F and G glycoproteins are also evident in their presentation of epitopes. Garcia-Barreno et al. (1989, J. Virol. 63:925–932), using panels of monoclonal antibodies, found that the epitopes of the F protein divided into five nonoverlapping groups, whereas the competition profiles of many of the epitopes on the G protein are extensively overlapped.

Recombinant vaccinia viruses containing a cDNA insert to the BRS virus F gene expressed the BRS virus F protein. This BRS virus F protein was cleaved into $F_1$ and $F_2$ polypeptides, and had an electraphoretic mobility in SDS-polyacrylamide gels which was similar to the F protein from BRS virus infected cells. Experiments with tunicamycin, an inhibitor of N-linked glycosylation, demonstrated that the BRS virus F protein expressed from recombinant infected cells was glycosylated to a level similar to the F proteins from BRS virus infected cells. The BRS virus F protein expressed from the recombinant vaccinia virus was transported to and expressed on the surface of infected cells as shown by surface immunofluorescence.

8. EXAMPLE

Production of Monospecific, Polyclonal Antibody to the BRS Virus G Protein and Demonstration of Antigenic Specificity To test the biological activity of the bovine RS virus attachment protein expressed from the recombinant VV vectors and to assess the antigenic cross-reactivity between the BRS and HRS virus G proteins using a polyclonal antisera, recombinant VV expressing either the BRS virus or HRS virus G protein were used to immunize animals as described in Stott et al., 1986, J. Virol. 60:607–613. Sera from animals immunized with the BRS virus G protein specifically immunoprecipitated the BRS virus attachment protein, but did not recognize the human RS virus G protein (FIG. 16). Similarly, antisera raised against the HRS virus G protein was specific for the HRS virus G protein and showed no recognition of the bovine RS virus G protein, confirming the antigenic distinctness of the two attachment proteins.

9. Deposit of Microorganisms

The following [microorganisms] were deposited with the American Type Culture Collection, Rockville, Md.

plasmid pRLG414-76-191 plasmid pRLF2012-76-1902 plasmid pRLNB3-76 virus rVG-642 virus rVF-464

The present invention is not limited in scope by the microorganisms deposited or the embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the scope of the Appended claims. A number of publications have been cited herein, which are incorporated by reference in their entirety.

SEQUENCE LISTING

```
<160> NUMBER OF SEQ ID NOS: 6

<210> SEQ ID NO 1
<211> LENGTH: 838
<212> TYPE: DNA
<213> ORGANISM: Bovine respiratory syncytial virus
<220> FEATURE:
<221> NAME/KEY: misc_feature
<222> LOCATION: (1)..(838)
<223> OTHER INFORMATION: n is a, c, t, or g

<400> SEQUENCE: 1
ngggcaaata caagtatgtc caaccatacc catcatctta aattcaagac attaaagagg      60
gcttggaaag cctcaaaata ctttatagta ggattatcat gtttatataa gttcaattta     120
aaatcccttg tccaaacggc tttgtccacc ctagcaatga taaccttgac atcactcgtc     180
atcacagcca ttatttacat tagtgtggga aatgctaaag ccaagcccac atccaaacca     240
accatccaac aaacacaaca gccccaaaac catacctcac cattttttcac agagcacaac    300 tacaaatcaa ctcacacatc aattcaaagc accacactgt cccaactact aaacatagac    360
actactagag gaattacata tggtcactca accaacgaaa cccaaaacag aaaaatcaaa    420
ggccaatcca ctctacccgc caccagaaaa ccaccaatca atccatcggg aagcatcccc    480
cctgaaaacc atcaagacca caacaacttc caaacactcc cctatgtgcc ttgcagtaca    540
tgtgaaggta atcttgcttg cttatcactc tgccatattg agacggagag agcaccaagc    600 agagcccta caatcaccct caaaaagact ccaaaaccca aaaccactaa aaagccaacc    660
aagacaacaa tccaccacag aaccagccct gaaaccaaac tgcaacctaa aaacaacaca    720
gcaactccac aacaaggcat cctctcttca acagaacatc acacaaatca atcaactaca    780
cagatctagc aacacacctc catataacat ctaattatng ttctatatat agttattt      838

<210> SEQ ID NO 2
<211> LENGTH: 257
<212> TYPE: PRT
<213> ORGANISM: Bovine respiratory syncytial virus
```

<400> SEQUENCE: 2

```
Met Ser Asn His Thr His His Leu Lys Phe Lys Thr Leu Lys Arg Ala
1               5                   10                  15

Trp Lys Ala Ser Lys Tyr Phe Ile Val Gly Leu Ser Cys Leu Tyr Lys
            20                  25                  30

Phe Asn Leu Lys Ser Leu Val Gln Thr Ala Leu Ser Thr Leu Ala Met
        35                  40                  45

Ile Thr Leu Thr Ser Leu Val Ile Thr Ala Ile Ile Tyr Ile Ser Val
50                  55                  60

Gly Asn Ala Lys Ala Lys Pro Thr Ser Lys Pro Thr Ile Gln Gln Thr
65                  70                  75                  80

Gln Gln Pro Gln Asn His Thr Ser Pro Phe Phe Thr Glu His Asn Tyr
                85                  90                  95

Lys Ser Thr His Thr Ser Ile Gln Ser Thr Thr Leu Ser Gln Leu Leu
            100                 105                 110

Asn Ile Asp Thr Thr Arg Gly Ile Thr Tyr Gly His Ser Thr Asn Glu
        115                 120                 125

Thr Gln Asn Arg Lys Ile Lys Gly Gln Ser Thr Leu Pro Ala Thr Arg
130                 135                 140

Lys Pro Pro Ile Asn Pro Ser Gly Ser Ile Pro Pro Glu Asn His Gln
145                 150                 155                 160

Asp His Asn Asn Phe Gln Thr Leu Pro Tyr Val Pro Cys Ser Thr Cys
                165                 170                 175

Glu Gly Asn Leu Ala Cys Leu Ser Leu Cys His Ile Glu Thr Glu Arg
            180                 185                 190

Ala Pro Ser Arg Ala Pro Thr Ile Thr Leu Lys Lys Thr Pro Lys Pro
        195                 200                 205

Lys Thr Thr Lys Lys Pro Thr Lys Thr Ile His His Arg Thr Ser
210                 215                 220

Pro Glu Thr Lys Leu Gln Pro Lys Asn Asn Thr Ala Thr Pro Gln Gln
225                 230                 235                 240

Gly Ile Leu Ser Ser Thr Glu His His Thr Asn Gln Ser Thr Thr Gln
                245                 250                 255

Ile
```

<210> SEQ ID NO 3
<211> LENGTH: 1899
<212> TYPE: DNA
<213> ORGANISM: Bovine respiratory syncytial virus
<220> FEATURE:
<221> NAME/KEY: misc_feature
<222> LOCATION: (1)..(257)
<223> OTHER INFORMATION: n is a, c, t, or g

<400> SEQUENCE: 3

```
nnnnnnnata aggatggcgg caacagccat gaggatgatc atcagcatta tcttcatctc    60
tacctatatg acacatatca ctttatgcca aaacataaca gaagaatttt atcaatcaac   120
atgcagtgca gttagtagag gttatcttag tgcattaaga actggatggt atacaagtgt   180
agtaacaata gagttgagca aaatacaaaa gaatgtgtgt aaaagtactg attcaaaagt   240
gaaattaata aagcaagaac tggaaagata caacaatgca gtaatagaat tgcagtcact   300
tatgcaaaat gaaccggctt ccttcagtag agcaaaaaga gggataccag agttgataca   360
ttatacaaga aactctacaa agagatttta tgggttaatg ggcaagaaga gaaagaggag   420
atttttagga ttcttgctag gtattggatc tgctgttgca agtggtgtag cagtgtccaa   480
```

-continued

```
agtactacac ctggagggag aggtgaataa aattaaaaat gcactgctat ccacaaataa      540
agcagtagtt agtctatcca atggagttag tgtccttact agcaaagtac ttgatctaaa      600
gaactatata gacaaagagc ttctacctaa agttaacaat catgattgta ggatatccaa      660
catagaaact gtgatagaat tccaacaaaa aaacaataga ttgttagaaa ttgctaggga      720
atttagtgta aatgctggta ttaccacacc cctcagtaca tacatgttga ccaatagtga      780
attactatca ctaattaatg atatgcctat aacgaatgac caaaaaaagc taatgtcaag      840
taatgttcaa atagtcagac aacagagtta ttccattatg tcagtggtca agaagaggt      900 catagcttat gttgtacaat tgcctattta tggagttata gacaccccct gttggaaact      960
acacacctct ccattatgca ccactgataa taaagaaggg tcaaacatct gcttaactag     1020
gacagatcgt gggtggtatt gtgacaatgc aggctctgtg tctttttcc cacaggcaga     1080 gacatgtaag gtacaatcaa atagagtgtt ctgtgcacaca atgaacagtt taactctgcc     1140
tactgatgtt aacttatgca acactgacat attcaataca agtatgact gtaaaataat      1200 gacatctaaa actgacataa gtagctctgt gataacttca ataggagcta ttgtatcatg      1260
ctatgggaag acaaaatgta cagcttctaa taaaaatcgt ggaatcataa agacttttc      1320 caatgggtgt gattatgtat caaacaaagg agttgacact gtatctgttg gtaacacact     1380
atattatgta aataagctag aggggaaagc actctatata aagggtgaac caattattaa     1440
ttactatgat ccactagtgt ttccttctga tgagtttgat gcatcaattg cccaagtaaa     1500
tgcaaaaata aaccaaagcc tggctttcat acgtcgatct gatgagttac ttcacagtgt     1560
agatgtagga aaatccacca caaatgtagt aattactact attattatag tgatagttgt     1620
agtgatatta atgttaatag ctgtaggatt actgttttac tgtaagacca ggagtactcc     1680
tatcatgcta ggaaaggatc agcttagtgg tatcaacaat cttcctttta gtaaatgaaa     1740
tgcataatgt ttacaatcta aacctcagaa tcataaatgt gatgagctaa atttattaat     1800
acattcaaaa gttctatccg ccaagacctg catttttta tcaggtctta tataagctaa      1860
ccttacatgc tacactcagc tccatgttga tagttatat                             1899
```

<210> SEQ ID NO 4
<211> LENGTH: 574
<212> TYPE: PRT
<213> ORGANISM: Bovine respiratory syncytial virus

<400> SEQUENCE: 4

```
Met Ala Ala Thr Ala Met Arg Met Ile Ile Ser Ile Ile Phe Ile Ser
1               5                   10                  15

Thr Tyr Met Thr His Ile Thr Leu Cys Gln Asn Ile Thr Glu Glu Phe
                20                  25                  30

Tyr Gln Ser Thr Cys Ser Ala Val Ser Arg Gly Tyr Leu Ser Ala Leu
            35                  40                  45

Arg Thr Gly Trp Tyr Thr Ser Val Val Thr Ile Glu Leu Ser Lys Ile
        50                  55                  60

Gln Lys Asn Val Cys Lys Ser Thr Asp Ser Lys Val Lys Leu Ile Lys
65                  70                  75                  80

Gln Glu Leu Glu Arg Tyr Asn Asn Ala Val Ile Glu Leu Gln Ser Leu
                85                  90                  95

Met Gln Asn Glu Pro Ala Ser Phe Ser Arg Ala Lys Arg Gly Ile Pro
            100                 105                 110

Glu Leu Ile His Tyr Thr Arg Asn Ser Thr Lys Arg Phe Tyr Gly Leu
```

-continued

```
            115                 120                 125
Met Gly Lys Lys Arg Lys Arg Arg Phe Leu Gly Phe Leu Gly Ile
    130                 135                 140
Gly Ser Ala Val Ala Ser Gly Val Ala Leu Ser Lys Val Leu His Leu
145                 150                 155                 160
Glu Gly Glu Val Asn Lys Ile Lys Asn Ala Leu Leu Ser Thr Asn Lys
                165                 170                 175
Ala Val Val Ser Leu Ser Asn Gly Val Ser Val Leu Thr Ser Lys Val
                180                 185                 190
Leu Asp Leu Lys Asn Tyr Ile Asp Lys Glu Leu Leu Pro Lys Val Asn
            195                 200                 205
Asn His Asp Cys Arg Ile Ser Asn Ile Glu Thr Val Ile Glu Phe Gln
    210                 215                 220
Gln Lys Asn Asn Arg Leu Leu Glu Ile Ala Arg Glu Phe Ser Val Asn
225                 230                 235                 240
Ala Gly Ile Thr Thr Pro Leu Ser Thr Tyr Met Leu Thr Asn Ser Glu
                245                 250                 255
Leu Leu Ser Leu Ile Asn Asp Met Pro Ile Thr Asn Asp Gln Lys Lys
            260                 265                 270
Leu Met Ser Ser Asn Val Gln Ile Val Arg Gln Gln Ser Tyr Ser Ile
            275                 280                 285
Met Ser Val Val Lys Glu Glu Val Ile Ala Tyr Val Val Gln Leu Pro
    290                 295                 300
Ile Tyr Gly Val Ile Asp Thr Pro Cys Trp Lys Leu His Thr Ser Pro
305                 310                 315                 320
Leu Cys Thr Thr Asp Asn Lys Glu Gly Ser Asn Ile Cys Leu Thr Arg
                325                 330                 335
Thr Asp Arg Gly Trp Tyr Cys Asp Asn Ala Gly Ser Val Ser Phe Phe
                340                 345                 350
Pro Gln Ala Glu Thr Cys Lys Val Gln Ser Asn Arg Val Phe Cys Asp
            355                 360                 365
Thr Met Asn Ser Leu Thr Leu Pro Thr Asp Val Asn Leu Cys Asn Thr
    370                 375                 380
Asp Ile Phe Asn Thr Lys Tyr Asp Cys Lys Ile Met Thr Ser Lys Thr
385                 390                 395                 400
Asp Ile Ser Ser Ser Val Ile Thr Ser Ile Gly Ala Ile Val Ser Cys
                405                 410                 415
Tyr Gly Lys Thr Lys Cys Thr Ala Ser Asn Lys Asn Arg Gly Ile Ile
                420                 425                 430
Lys Thr Phe Ser Asn Gly Cys Asp Tyr Val Ser Asn Lys Gly Val Asp
            435                 440                 445
Thr Val Ser Val Gly Asn Thr Leu Tyr Tyr Val Asn Lys Leu Glu Gly
450                 455                 460
Lys Ala Leu Tyr Ile Lys Gly Glu Pro Ile Ile Asn Tyr Tyr Asp Pro
465                 470                 475                 480
Leu Val Phe Pro Ser Asp Glu Phe Asp Ala Ser Ile Ala Gln Val Asn
                485                 490                 495
Ala Lys Ile Asn Gln Ser Leu Ala Phe Ile Arg Arg Ser Asp Glu Leu
                500                 505                 510
Leu His Ser Val Asp Val Gly Lys Ser Thr Thr Asn Val Val Ile Thr
            515                 520                 525
Thr Ile Ile Ile Val Ile Val Val Ile Leu Met Leu Ile Ala Val
            530                 535                 540
```

Gly Leu Leu Phe Tyr Cys Lys Thr Arg Ser Thr Pro Ile Met Leu Gly
545                 550                 555                 560

Lys Asp Gln Leu Ser Gly Ile Asn Asn Leu Ser Phe Ser Lys
            565                 570

<210> SEQ ID NO 5
<211> LENGTH: 396
<212> TYPE: PRT
<213> ORGANISM: Bovine respiratory syncytial virus

<400> SEQUENCE: 5

Lys Met Ala Leu Ser Lys Val Lys Leu Asn Asp Thr Phe Asn Lys Asp
1               5                   10                  15

Gln Leu Leu Ser Thr Ser Lys Tyr Thr Ile Gln Arg Ser Thr Gly Asp
            20                  25                  30

Asn Ile Asp Ile Pro Asn Tyr Asp Val Gln Lys His Leu Asn Lys Leu
        35                  40                  45

Cys Gly Met Leu Leu Ile Thr Glu Asp Ala Asn His Lys Phe Thr Gly
    50                  55                  60

Leu Ile Gly Met Leu Tyr Ala Met Ser Arg Leu Gly Arg Glu Asp Thr
65                  70                  75                  80

Leu Lys Ile Leu Lys Asp Ala Gly Tyr Gln Val Arg Ala Asn Gly Val
                85                  90                  95

Asp Val Ile Thr His Arg Gln Asp Val Asn Gly Lys Glu Met Lys Phe
            100                 105                 110

Glu Val Leu Thr Leu Val Ser Leu Thr Ser Glu Val Gln Gly Asn Ile
        115                 120                 125

Glu Ile Glu Ser Arg Lys Ser Tyr Lys Lys Met Leu Lys Glu Met Gly
    130                 135                 140

Glu Val Ala Pro Glu Tyr Arg His Asp Phe Pro Asp Cys Gly Met Ile
145                 150                 155                 160

Val Leu Cys Val Ala Ala Leu Val Ile Thr Lys Leu Ala Ala Gly Asp
                165                 170                 175

Arg Ser Gly Leu Thr Ala Val Ile Arg Arg Ala Asn Asn Val Leu Arg
            180                 185                 190

Asn Glu Met Lys Arg Tyr Lys Gly Leu Ile Pro Lys Asp Ile Ala Asn
        195                 200                 205

Ser Phe Tyr Glu Val Phe Glu Lys Tyr Pro His Tyr Ile Asp Val Phe
    210                 215                 220

Val His Phe Gly Ile Ala Gln Ser Ser Thr Arg Gly Gly Ser Arg Val
225                 230                 235                 240

Glu Gly Ile Phe Ala Gly Leu Phe Met Asn Ala Tyr Gly Ala Gly Gln
                245                 250                 255

Val Met Leu Arg Trp Gly Val Leu Ala Lys Ser Val Lys Asn Ile Met
            260                 265                 270

Leu Gly His Ala Ser Val Gln Ala Glu Met Glu Gln Val Val Glu Val
        275                 280                 285

Tyr Glu Tyr Ala Gln Lys Leu Gly Gly Glu Ala Gly Phe Tyr His Ile
    290                 295                 300

Leu Asn Asn Pro Lys Ala Ser Leu Leu Ser Leu Thr Gln Phe Pro Asn
305                 310                 315                 320

Phe Ser Ser Val Val Leu Gly Asn Ala Ala Gly Leu Gly Ile Met Gly
                325                 330                 335

Glu Tyr Arg Gly Thr Pro Arg Asn Gln Asp Leu Tyr Asp Ala Ala Lys

```
                340                 345                 350
Ala Tyr Ala Glu Gln Leu Lys Glu Asn Gly Val Ile Asn Tyr Ser Val
                355                 360                 365

Leu Asp Leu Thr Thr Glu Glu Leu Glu Ala Ile Lys Asn Gln Leu Asn
        370                 375                 380

Pro Lys Asp Asn Asp Val Glu Leu Val Asn Lys Lys
385                 390                 395

<210> SEQ ID NO 6
<211> LENGTH: 1194
<212> TYPE: DNA
<213> ORGANISM: Bovine respiratory syncytial virus

<400> SEQUENCE: 6
caaaaatggc tcttagcaag gtcaaactaa atgacacttt caacaaggac caactgttgt      60
caaccagcaa atatactatt caacgtagta caggtgacaa cattgatata cccaattacg     120
atgtgcaaaa acatctcaat aagttgtgtg gtatgctatt aataacagaa gatgccaatc     180
ataaatttac aggactgata ggtatgttat atgctatgtc ccgattgggg agagaagata     240
cccttaaaat actcaaagat gcaggctacc aagtgagggc caatggggtt gatgtgataa     300
cacatcgaca ggatgtgaat ggaaaagaaa tgaaatttga agtgctaaca ttagtcagct     360
taacatcaga agttcaaggt aatatagaaa tagagtcaag gaagtcttac aaaaagatgc     420
taaaagagat gggagaggta gctccagaat acagacatga ctctcctgat tgtggtatga     480
tagtgctatg tgttgctgct ttggttataa caaaattagc agcaggtgat aggtcaggcc     540
tcactgcagt cattaggaga gccaacaatg tactaaggaa tgaaatgaaa cgatacaaag     600
gactcatccc gaaagatata gccaacagct tctatgaagt atttgaaaag taccctcatt     660
acatagatgt attcgtacat tttggcattg ctcaatcctc aactagagga ggtagtaggg     720
tagaaggaat cttttgcaggg ttattcatga atgcatatg agcaggtcaa gtgatgttaa     780 gatgggtgt actagccaaa tcagtcaaga atattatgct tggtcatgcc agcgtacaag     840
cagaaatgga acaggttgta gaagtctatg aatatgcaca aaagttaggt ggagaagctg     900
gtttttatca catactgaac aaccctaaag catcattgtt atccttaaca caattcccca     960
atttctctag tgtagtccta ggcaatgctg caggactagg tataatgggt gagtatagag    1020
gtacaccaag aaaccaagac ttgtatgatg ctgccaaagc atatgcagaa caactaaaag    1080
agaatggggt catcaattac agtgtattgg atctgactac agaggaatta gaggcaatca    1140
agaaccaatt gaatcccaaa gataatgatg tggaattgtg agttaataaa aaaa          1194
```

What is claimed is:

1. A vaccine composition comprising a suitable pharmaceutical vehicle and at least one immunogenic bovine respiratory syncytial virus (BRSV) protein selected from the group consisting of immunogenic fragments of BRSV G, immunogenic fragments of BRSV F and immunogenic fragments of BRSV N.

2. The vaccine composition of claim 1 wherein said protein is immunogenic fragments of BRSV G, immunogenic fragments of BRSV F, and immunogenic fragments of BRSV N.

3. A method of treating or preventing bovine respiratory syncytial virus infection in a bovine subject comprising administering to said subject a therapeutically effective amount of a vaccine composition according to claim 2.

* * * * *

UNITED STATES PATENT AND TRADEMARK OFFICE
CERTIFICATE OF CORRECTION

PATENT NO. : 6,730,305 B1
DATED : May 4, 2004
INVENTOR(S) : Wertz et al.

It is certified that error appears in the above-identified patent and that said Letters Patent is hereby corrected as shown below:

Title page,
Item [56], References Cited, OTHER PUBLICATIONS, "Van Regenmortel (Ed.)" reference, "vol." should be replaced with -- Vol. --.

Column 3,
Line 67, "orvell" should be replaced with -- Orvell --.

Column 29,
Line 62, "IRS" should be replaced with -- HRS --.

Column 31,
Line 3, "HS" should be replaced with -- HRS --.

Signed and Sealed this

Thirtieth Day of August, 2005

JON W. DUDAS
*Director of the United States Patent and Trademark Office*